US012740752B2

(12) United States Patent
Ryu

(10) Patent No.: US 12,740,752 B2
(45) Date of Patent: Sep. 22, 2026

(54) X-RAY DETECTOR, METHOD FOR OPERATING X-RAY DETECTOR, AND X-RAY IMAGING DEVICE INCLUDING X-RAY DETECTOR

(71) Applicant: Samsung Electronics Co., Ltd., Suwon-si (KR)

(72) Inventor: Jeaeun Ryu, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 116 days.

(21) Appl. No.: 18/627,165

(22) Filed: Apr. 4, 2024

(65) Prior Publication Data

US 2024/0245367 A1 Jul. 25, 2024

Related U.S. Application Data

(63) Continuation of application No. PCT/KR2022/015271, filed on Oct. 11, 2022.

(30) Foreign Application Priority Data

Oct. 18, 2021 (KR) ........................ 10-2021-0138841

(51) Int. Cl.
*A61B 6/42* (2024.01)
*A61B 6/00* (2024.01)

(52) U.S. Cl.
CPC ............ *A61B 6/4208* (2013.01); *A61B 6/542* (2013.01)

(58) Field of Classification Search
CPC ..... A61B 6/4208; A61B 6/542; A61B 6/5433; A61B 6/4405
See application file for complete search history.

(56) References Cited

U.S. PATENT DOCUMENTS 5,693,948 A 12/1997 Sayed et al.
6,343,112 B1 * 1/2002 Petrick .................. A61B 6/482 378/207

(Continued)

FOREIGN PATENT DOCUMENTS

EP 1 642 529 A1 4/2006
JP 2002-243860 8/2002

(Continued)

OTHER PUBLICATIONS

Extended European Search Report dated Nov. 11, 2024 issued in European Patent Application No. 22883846.2.

(Continued)

*Primary Examiner* — Casey Bryant
(74) *Attorney, Agent, or Firm* — Nixon & Vanderhye P.C.

(57) ABSTRACT

Provided are an X-ray detector, a method, performed by the X-ray detector, of variably adjusting a window time of the X-ray detector, and an X-ray imaging device including the X-ray detector. The X-ray detector according to an embodiment of the present disclosure may obtain information about an X-ray emission end time point based on an X-ray emission end signal received from an automatic exposure control (AEC) device or a setting value for an X-ray emission time received from a workstation, adjust a window time based on the information about the X-ray emission end time point, and in response to the window time being ended, obtain X-ray image data by performing a readout.

15 Claims, 15 Drawing Sheets

(56) References Cited

U.S. PATENT DOCUMENTS

| | | | |
|---|---|---|---|
| 8,637,832 B2 | 1/2014 | Watanabe | |
| 9,146,326 B2 | 9/2015 | Kuwabara | |
| 9,579,076 B2 | 2/2017 | Tajima | |
| 9,774,794 B2 | 9/2017 | Sakino | |
| 10,307,117 B2 | 6/2019 | Park | |
| 11,067,706 B2 | 7/2021 | Furumoto | |
| 2015/0055751 A1 | 2/2015 | Funk et al. | |
| 2015/0055752 A1* | 2/2015 | Takahashi | H04N 25/67 378/91 |
| 2015/0230324 A1* | 8/2015 | Kuwabara | A61B 6/542 378/108 |
| 2017/0056688 A1 | 3/2017 | Penfold | |

FOREIGN PATENT DOCUMENTS

| | | | |
|---|---|---|---|
| JP | 2007213979 | A | 8/2007 |
| JP | 2010033822 | A | 2/2010 |
| JP | 2011234915 | A | 11/2011 |
| JP | 2013233420 | A | 11/2013 |
| JP | 5556367 | B2 | 6/2014 |
| JP | 2016-116754 | | 6/2016 |
| KR | 20170089243 | A | 8/2017 |
| KR | 20180046939 | A | 5/2018 |
| KR | 102181595 | B1 | 11/2020 |

OTHER PUBLICATIONS

Muddiman, Ryan, A quantitative study of image lag in flat-panel fluoroscopy systems,, [URL : https://www.researchgate.net/ publication/ 348735456_A_quantitative_study_of_image_lag_in_flat-panel_fluoroscopy_systems], pp. 1-54, Sep. 9, 2020.

International Search Report and Written Opinion of the ISA for PCT/KR2022/015271 mailed Jan. 18, 2023, 9 pages.

European Notice of Allowance issued Apr. 17, 2025 in corresponding European Patent Application No. 22883846.2.

Korean Office Action dated Jul. 2, 2026 for KR Application No. 10-2021-0138841.

* cited by examiner

X-RAY DETECTOR, METHOD FOR OPERATING X-RAY DETECTOR, AND X-RAY IMAGING DEVICE INCLUDING X-RAY DETECTOR

CROSS-REFERENCE TO RELATED APPLICATIONS

This application is a continuation of International Application No. PCT/KR2022/015271 designating the United States, filed on Oct. 11, 2022, in the Korean Intellectual Property Receiving Office and claiming priority to Korean Patent Application No. 10-2021-0138841, filed on Oct. 18, 2021, in the Korean Intellectual Property Office, the disclosures of each of which are incorporated by reference herein in their entireties.

BACKGROUND

Field

The disclosure relates to an X-ray detector, an operation method of the X-ray detector, and an X-ray imaging device including the X-ray detector. For example, the present disclosure relates to an X-ray detector for dynamically adjusting a window time for receiving X-rays that have passed through an object, a method, performed by the X-ray detector, of dynamically adjusting a window time, and an X-ray imaging device including the X-ray detector.

Description of Related Art

X-rays are electromagnetic waves having wavelengths of 0.01 to 100 angstroms (Å), and may be widely used, due to their ability to pass through objects, in medical devices for imaging the inside of a living body or in non-destructive testing equipment for industrial use.

An X-ray imaging device using X-rays is basically for examining an internal structure of an object by transmitting X-rays emitted from an X-ray tube (or an X-ray source), through the object and detecting a difference in intensities of the transmitted X-rays using an X-ray detector.

Recently, an X-ray detector including a flat-panel detector (FPD) is widely used wherein the FPD is configured to detect, using a thin-film transistor (TFT) active matrix substrate in which a plurality of pixels are arranged to accumulate signal charges according to the amount of incident X-rays, X-ray signals by accumulating signal charges in each of the plurality of pixels of the TFT active matrix substrate, and obtain X-ray image data of the object using the detected X-ray signals. Because it is difficult to specify the output characteristics of a high-voltage generator (HVG) configured to apply a high voltage to an X-ray source, an X-ray imaging device for obtaining an X-ray image of an object using an X-ray detector performs X-ray imaging using a window time of the X-ray detector, which is fixed to a preset value, or using a static window time that is set according to the characteristics of the object (e.g., a patient's age, the type of the object, or the thickness of the object). For example, the X-ray imaging device performs X-ray imaging by setting a time period during which the X-ray detector receives X-rays that have passed through an object, to any one of 550 ms, 1050 ms, or 2050 ms.

In general, a setting value for a window time of an X-ray detector is greater than a time period during which X-rays are actually emitted. For example, an X-ray emission time is about 10 ms in a chest anterior-posterior (AP) protocol for imaging a patient's chest, is about 50 ms in a protocol for imaging a patient's hands or feet, and is about 100 ms in a pelvis protocol for imaging a patient's pelvis. Thus, in a case in which the window time of the X-ray detector is set to 550 ms, an unnecessary waste of time occurs even though X-rays are not actually emitted, a time point for an X-ray image confirmation may be delayed, and the processing time may be increased.

In addition, as the window time increases, noise due to a dark current in a photo sensor (e.g., an amorphous-Si-based TFT or a PIN diode) of the X-ray detector may be increased.

SUMMARY

An example embodiment of the present disclosure provides a method of variably adjusting a window time of an X-ray detector. An method of operating an X-ray detector according to an example embodiment of the present disclosure may include: obtaining information about an X-ray emission end time point based on an X-ray emission end signal received from an automatic exposure control (AEC) device or a setting value for an X-ray emission time received from a workstation; adjusting a window time for the X-ray detector to receive X-rays that have passed through an object, based on the information about the X-ray emission end time point; and in response to the window time being ended, obtaining X-ray image data by performing a readout.

An example embodiment of the present disclosure provides an X-ray detector configured to variably adjusting a window time. An X-ray detector according to an example embodiment of the present disclosure may include: an X-ray receiver configured to detect X-rays that have passed through an object, and converting the detected X-rays into electric signals, a communication interface comprising circuitry configured to perform data communication with an automatic exposure control (AEC) device, a high-voltage generator (HVG), or a workstation, a memory storing at least one instruction, and at least one processor, comprising processing circuitry, individually and/or collectively, configured by executing the at least one instruction stored in the memory to: obtain information about an X-ray emission end time point based on an X-ray emission end signal received from the AEC device through the communication interface, or a setting value for an X-ray emission time received from the workstation; adjust a window time for the X-ray detector to receive X-rays that have passed through the object, based on the information about the X-ray emission end time point; and in response to the window time being ended, obtain X-ray image data by performing a readout.

An example embodiment of the present disclosure provides a computer program product including a non-transitory computer-readable storage medium having recorded thereon a program to be executed by a computer.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
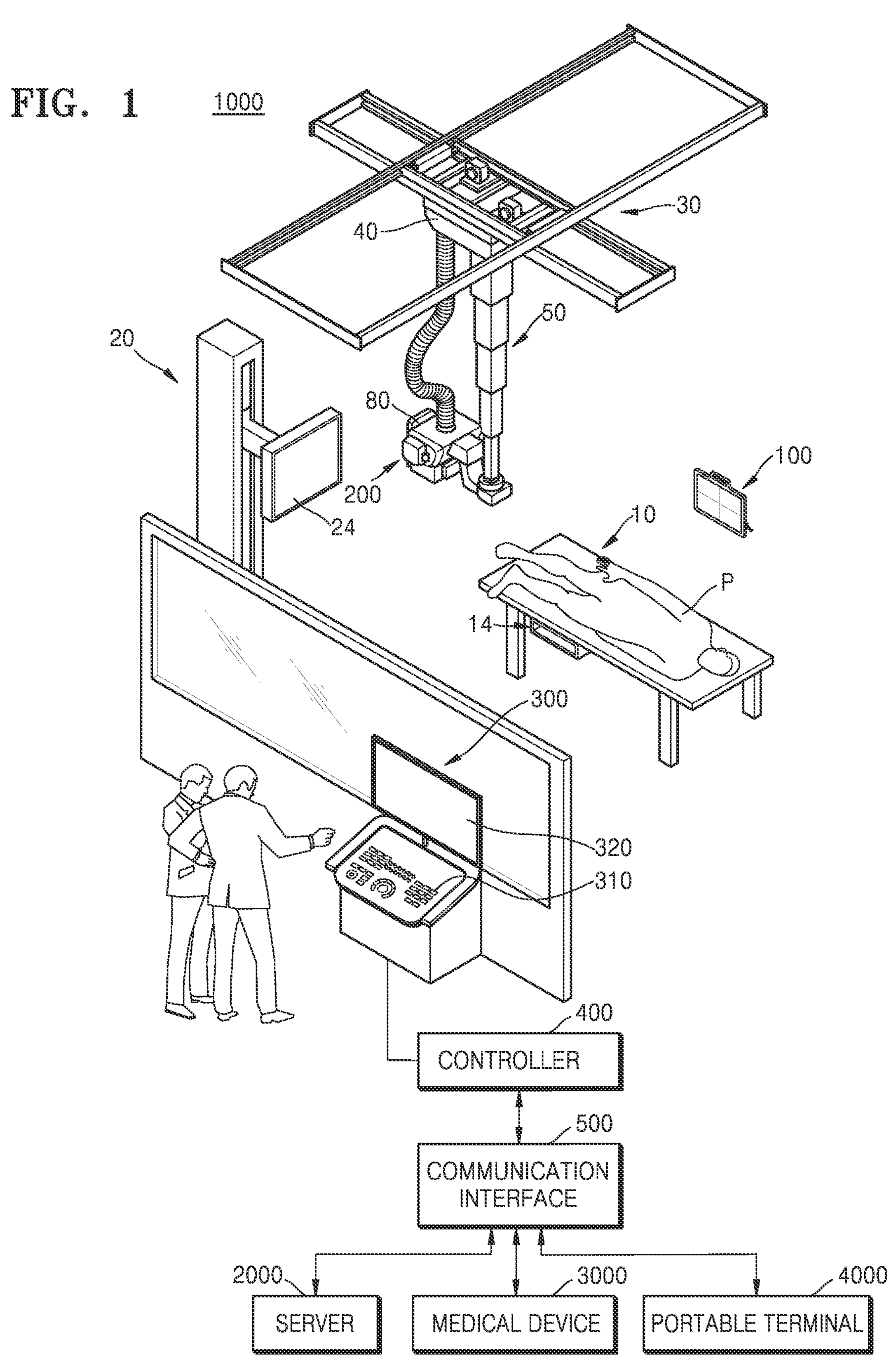
FIG. 1 is a diagram illustrating an example configuration of an X-ray imaging device according to various embodiments.

Although the terms used herein are selected from among common terms that are currently widely used in consideration of their function in the present disclosure, the terms may be different according to an intention of those of ordinary skill in the art, a precedent, or the advent of new technology. Also, in particular cases, the terms may be arbitrarily selected, in which case, the meaning of those terms will be described in detail in the corresponding description. Therefore, the terms used herein are not merely designations of the terms, but the terms are defined based on the meaning of the terms and content throughout the present disclosure.

The singular expression may also include the plural meaning as long as it is not inconsistent with the context. All the terms used herein, including technical and scientific terms, may have the same meanings as those generally understood by those of skill in the art.

Throughout the present disclosure, when a part "includes" an element, it is to be understood that the part may additionally include other elements rather than excluding other elements as long as there is no particular opposing recitation. In addition, as used herein, the terms such as ". . . er (or)", ". . . unit", ". . . module", etc., denote a unit that performs at least one function or operation, which may be implemented as hardware or software or a combination thereof.

As used herein, the expression "configured to" may be interchangeably used with, for example, "suitable for", "having the capacity to", "designed to", "adapted to", "made to", or "capable of", according to a situation. The expression "configured to" may not imply only "specially designed to" in a hardware manner. Instead, in a certain circumstance, the expression "a system configured to" may indicate the system "capable of" together with another device or components. For example, "a processor configured (or set) to perform A, B, and C" may imply a dedicated processor (e.g., an embedded processor) for performing a corresponding operation or a generic-purpose processor (e.g., central processing unit (CPU) or an application processor) capable of performing corresponding operations by executing one or more software programs stored in a memory.

In addition, in the present disclosure, it should be understood that when components are "connected" or "coupled" to each other, the elements may be directly connected or coupled to each other, but may alternatively be connected or coupled to each other with an element therebetween, unless specified otherwise.

In the present disclosure, the term 'object' refers to a target to be photographed, and may include a person, an animal, or part thereof. For example, an object may include part of a human body (e.g., an organ), a phantom, and the like.

In the present disclosure, X-rays may refer, for example, to electromagnetic waves having wavelengths of 0.01 to 100 angstroms (Å), and may be widely used, due to their ability to pass through objects, in medical devices for imaging the inside of a living body or in non-destructive testing equipment for industrial use.

In the present disclosure, an 'X-ray detector' may refer, for example, to a device configured to detect X-rays that have been emitted by an X-ray source (or an X-ray tube) and passed through an object, convert the detected X-rays into electric signals, and measure the electric signals. In an embodiment, the X-ray detector may be an indirect-type detector configured to convert X-rays that have passed through an object into visible light, and measure signals by electron-hole pairs generated by the visible light. However, the present disclosure is not limited thereto, and an X-ray detector according to an embodiment of the present disclosure may be a direct-type detector configured to generate electron-hole pairs directly from X-rays without converting the X-rays into visible light, and measure signals by the electron-hole pairs.

Hereinafter, various example embodiments of the present disclosure will be described in greater detail with reference to the accompanying drawings. The present disclosure may however, be embodied in many different forms and should not be construed as being limited to any embodiment set forth herein.

Hereinafter, various example embodiments of the present disclosure will be described in greater detail with reference to the drawings.

FIG. 1 is a diagram view illustrating an example configuration of an X-ray imaging device 1000 according to various embodiments. An example of a stationary X-ray imaging device will be described with reference to FIG. 1.

Referring to FIG. 1, the X-ray imaging device 1000 may include an X-ray detector 100 configured to detect X-rays that have passed through an object P, an X-ray emitter 200 configured to generate X-rays and emit the X-rays toward the object P, and a workstation 300 configured to receive a command from a user and provide information to the user. In addition, the X-ray imaging device 1000 may include a controller (e.g., including various control/processing circuitry) 400 configured to control the X-ray imaging device 1000 according to an input command, and a communication interface (e.g., including circuitry) 500 configured to communicate with an external device.

Some or all of the components of the controller 400 and the communication interface 500 may be included in the workstation 300 or may be provided separately from the workstation 300.

The X-ray emitter 200 may include an X-ray source configured to generate X-rays, and a collimator configured to adjust an emission area of the X-rays generated by the X-ray source.

A guide rail 30 may be installed on the ceiling of an examination room where the X-ray imaging device 1000 is arranged, the X-ray emitter 200 may be connected to a moving carriage 40 that moves along the guide rail 30, such that the X-ray emitter 200 may be moved to a position corresponding to the object P, and the moving carriage 40 and the X-ray emitter 200 may be connected to each other through a foldable post frame 50 to adjust the height of the X-ray emitter 200.

The workstation 300 may include an input interface 310 configured to receive a command from the user, and a display 320 configured to display information.

The input interface 310 may receive a command for controlling an imaging protocol, imaging conditions, an imaging timing, the position of the X-ray emitter 200, and the like. The input interface 310 may include various circuitry, including, for example, and without limitation, a keyboard, a mouse, a touch screen, a speech recognizer, and the like.

The display 320 may display a screen image for providing the user with a guide to making an input, an X-ray image, a screen image showing the state of the X-ray imaging device 1000, and the like.

The controller 400 may include various control/processing circuitry and control an imaging timing and imaging conditions of the X-ray emitter 200 according to a command input from the user, and may generate a medical image using image data received from the X-ray detector 100. In addition, the controller 400 may control the position or posture of a mounting unit 14 or 24 on which the X-ray emitter 200 or the X-ray detector 100 is mounted, according to the imaging protocol and the position of the object P.

The controller 400 may include a memory storing a program for performing the operations described above and operations to be described below, and at least one processor, comprising processing circuitry, configured to execute the stored program. The controller 400 may include a single processor or a plurality of processors, and in the latter case, the plurality of processors may be integrated on one chip or may be physically separated from each other. The processor according to an embodiment of the disclosure may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

The X-ray imaging device 1000 may be connected to an external device (e.g., an external server 2000, a medical device 3000, or a portable terminal 4000 (e.g., a smart phone, a tablet personal computer (PC), or a wearable device)) and configured to transmit and receive data to and from the external device.

The communication interface 500 may include one or more components including various circuitry configured to enable communication with the external device, and may include, for example, at least one of a short-range communication module, a wired communication module, and a wireless communication module.

In addition, the communication interface 500 may receive a control signal from the external device and transmit the received control signal to the controller 400 such that the controller 400 controls the X-ray imaging device 1000 according to the received control signal.

In addition, the controller 400 may transmit a control signal to the external device through the communication interface 500, to control the external device according to the control signal of the controller 400. For example, the external device may process data of the external device according to a control signal received from the controller 400 through the communication interface 500.

In addition, the communication interface 500 may further include an internal communication module including various communication circuitry configured to enable communication between components of the X-ray imaging device 1000. A program for controlling the X-ray imaging device 1000 may be installed in the external device, and the program may include instructions for performing some or all of operations of the controller 400.

The program may include various executable program instructions and be pre-installed in the portable terminal 4000, or a user of the portable terminal 4000 may download and install the program from a server for providing applications. The server for providing applications may include a recording medium storing the program.

In addition, the X-ray detector 100 may be implemented as a fixed X-ray detector fixed to a stand 20 or a table 10, or may be implemented as a portable X-ray detector that may be detachably mounted on the mounting unit 14 or 24 and may be used in any location. The portable X-ray detector may be implemented as a wired or wireless type depending on a data transmission method and a power supply method.

The X-ray detector 100 may or may not be included in the X-ray imaging device 1000 as a component. In the latter case, the X-ray detector 100 may be registered in the X-ray imaging device 1000 by the user. In addition, in both cases, the X-ray detector 100 may be connected to the controller 400 through the communication interface 500 to receive a control signal or transmit image data from or to the controller 400.

A sub-user interface 80 may include various circuitry configured to provide information to the user and receive a command from the user may be provided on one side of the X-ray emitter 200, and some or all of functions performed by the input interface 310 and the display 320 of the workstation 300 may be performed by the sub-user interface 80.

In a case in which all or some of the components of the controller 400 and the communication interface 500 are provided separately from the workstation 300, they may be included in the sub-user interface 80 provided in the X-ray emitter 200.

Although FIG. 1 illustrates the stationary X-ray imaging device 1000 connected to the ceiling of the examination room, the X-ray imaging device 1000 may include X-ray devices of various structures within the range that will be apparent to those of skill in the art, such as a C-arm-type X-ray device or a mobile X-ray device.

Figure 2:
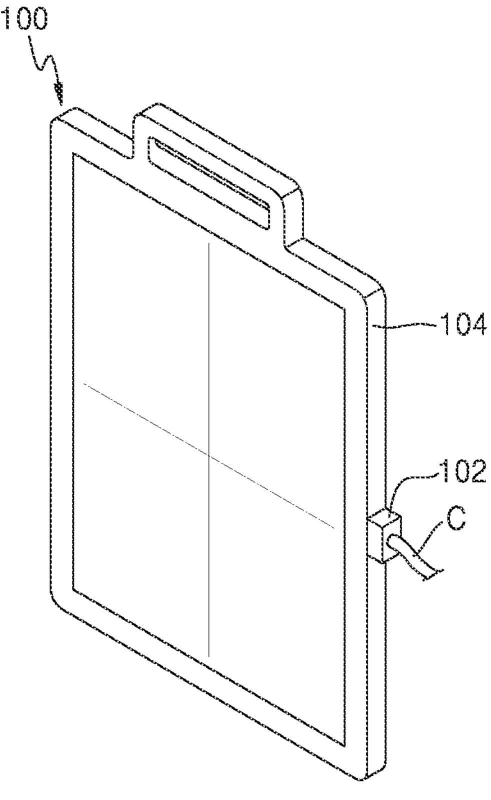
FIG. 2 is a perspective view illustrating an X-ray detector according to various embodiments.

FIG. 2 is a perspective view of the X-ray detector 100 according to various embodiments.

Referring to FIG. 2, the X-ray detector 100 may be implemented as a mobile X-ray detector. In this case, the X-ray detector 100 may include a battery to supply power so as to operate wirelessly, and as illustrated in FIG. 2, the X-ray detector 100 may operate with a charging port 102 connected to a separate power supply through a cable C.

A detection element may include various circuitry configured to detect X-rays and convert the detected X-rays into image data, a memory for temporarily or non-temporarily storing the image data, a communication module configured to receive a control signal from the X-ray imaging device 1000 or transmit image data to the X-ray imaging device 1000, and a battery may be provided inside a case 104 that forms the exterior of the X-ray detector 100. In addition, image correction information of the detector and unique identification information of the X-ray detector 100 may be stored in the memory, and the stored identification information may be transmitted when communicating with the X-ray imaging device 1000.

Figure 3:
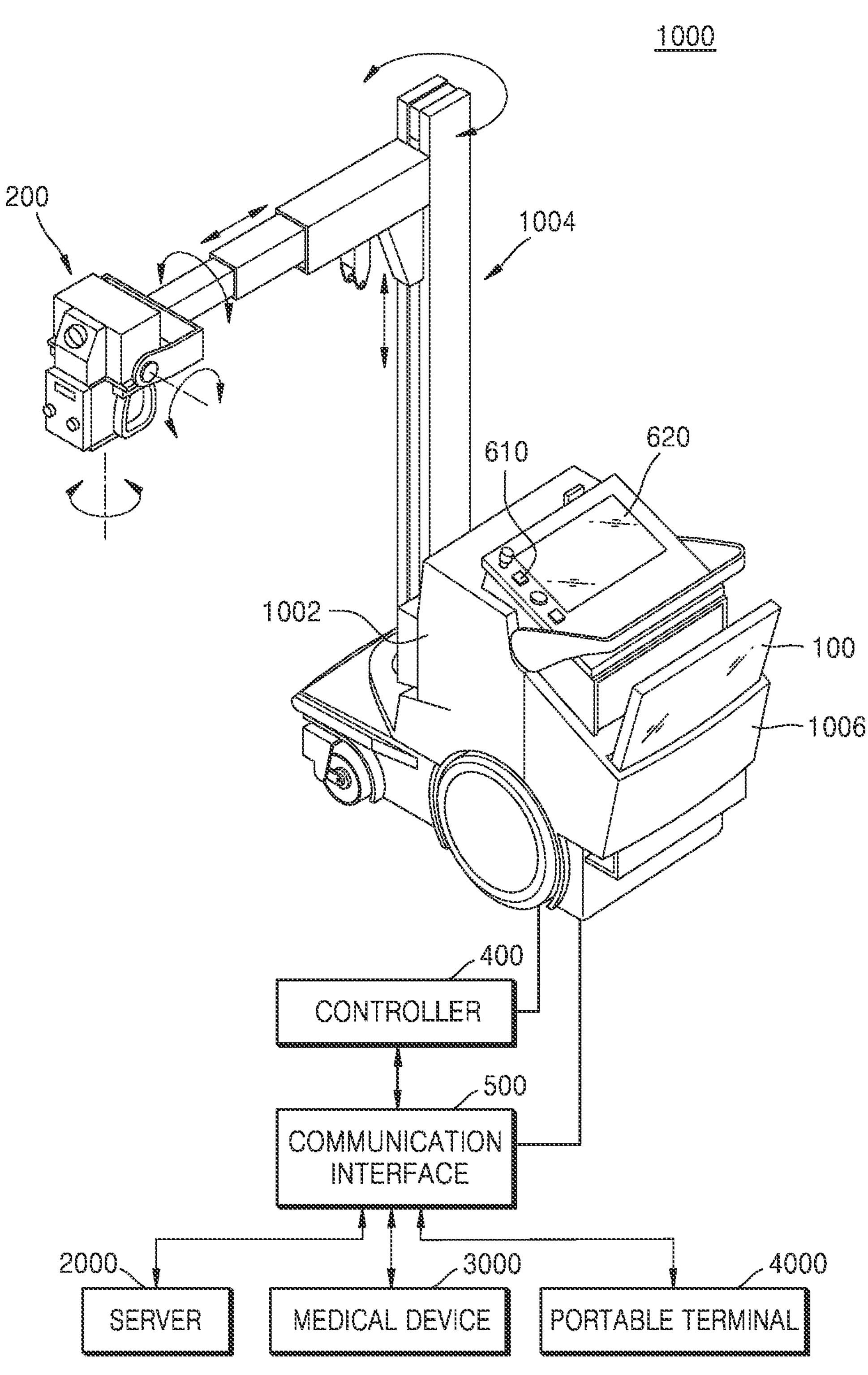
FIG. 3 is an diagram illustrating an X-ray device according to various embodiments.

FIG. 3 is a diagram illustrating an example mobile X-ray device as an example of the X-ray imaging device 1000 according to various embodiments.

A component corresponding to the same reference numeral as in FIG. 1 performs the same or similar function as the component in FIG. 1, and thus, redundant descriptions thereof provided above with reference to FIG. 1 may not be repeated here.

The X-ray imaging device 1000 may be implemented not only as the ceiling type described above but also as a mobile type. In a case in which the X-ray imaging device 1000 is implemented as a mobile X-ray device, because a main body 1002 to which the X-ray emitter 200 is connected is movable freely, and an arm 1004 connecting the X-ray emitter 200 to the main body 1002 is capable of rotation and straight movement, the X-ray emitter 200 may be freely moved in a three-dimensional space.

The main body 1002 may include a storage 1006 to store the X-ray detector 100. In addition, a charging port for charging the X-ray detector 100 may be provided inside the storage 1006, such that the storage 1006 may simultaneously charge and store the X-ray detector 100.

The controller 400, the communication interface 500, an input interface 610, and an outputter 620 may be provided in the main body 1002, and image data obtained by the X-ray detector 100 may be transmitted to the main body 1002 to undergo image processing and then be displayed on the outputter 620 or transmitted to an external device through the communication interface 500.

In addition, the controller 400 and the communication interface 500 may be provided separately from the main body 1002, and some of the components of the controller 400 and the communication interface 500 may be provided in the main body 1002.

Figure 4:
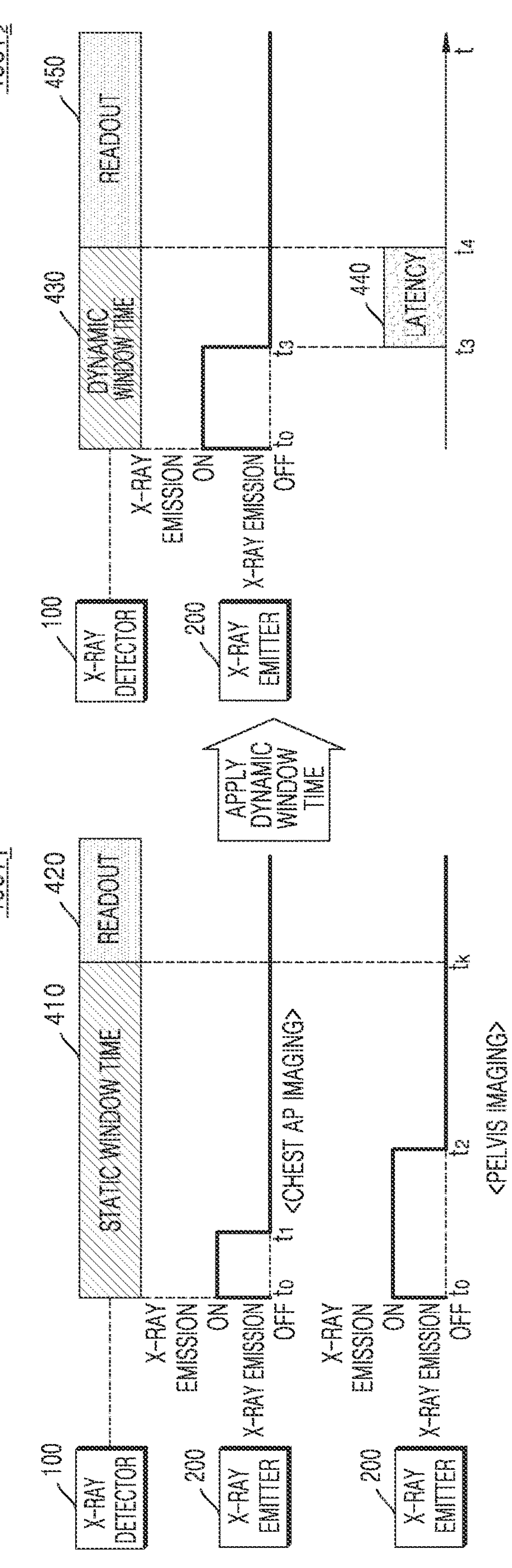
FIG. 4 is a diagram illustrating example timing charts each illustrating a window time changed as a dynamic window time is applied by an X-ray detector, according to various embodiments.

FIG. 4 is a diagram illustrating example timing charts 400$T_1$ and 400$T_2$ each illustrating a window time changed as a dynamic window time is applied by an X-ray detector, according to various embodiments.

Referring to the first timing chart 400$T_1$, during a preset static window time 410, the X-ray detector 100 receives X-rays that have passed through an object. The static window time 410 may be a default time that is set by an X-ray imaging device, or may be a time that is set by a user. In the embodiment illustrated in FIG. 4, the static window time 410 may be a time from an X-ray emission start time point $t_0$ to a k-th time point $t_k$. For example, the static window time 410 may be 550 ms, but is not limited thereto.

The X-ray detector 100 obtains X-ray image data about the object by performing a readout at the k-th time point $t_k$ at which the static window time 410 ends. In an embodiment, during a readout time 420, the X-ray detector 100 may release charges accumulated in a PIN diode in a photo sensor 114 (see FIG. 5) and perform read-out for converting the released charges into X-ray image data.

The X-ray emitter 200 may generate X-rays by receiving a high voltage generated by a high-voltage generator (HVG), and emit the generated X-rays toward an object. The X-ray emitter 200 may include an X-ray source configured to emit X-rays, and a collimator configured to control an emission area of the X-rays emitted by the X-ray source by guiding the X-rays to a path. In an embodiment, the X-ray emitter 200 may emit X-rays during an X-ray emission time that is set according to a control signal received from the workstation 300 (see FIG. 1) or the controller 400 (see FIG. 1). In an embodiment, the X-ray emission time may be determined according to an imaging protocol (e.g., an anatomically programmed radiography (APR) protocol). In the embodiment illustrated in FIG. 4, in a case of, for example, a chest anterior-posterior (AP) protocol for imaging a patient's chest, the X-ray emitter 200 may emit X-rays during a time from the X-ray emission start time point $t_0$ to a first time point $t_1$. For example, in the case of the chest AP protocol, the X-ray emission time (e.g., from $t_0$ to $t_1$) may be 10 ms. As another example, in a case of, for example, a pelvis protocol for imaging a patient's pelvis, the X-ray emitter 200 may emit X-rays during a time from the X-ray emission start time point $t_0$ to a second time point $t_2$, and in this case, the X-ray emission time (e.g., from $t_0$ to $t_2$) may be 100 ms. However, the X-ray emission time according to the imaging protocol is not limited to 10 ms or 100 ms.

Referring to the second timing chart 400$T_2$, during a dynamic window time 430, the X-ray detector 100 receives X-rays that have passed through an object. The dynamic window time 430 may be a time interval that is dynamically adjusted by the X-ray detector 100. In the embodiment illustrated in FIG. 4, the dynamic window time 430 may refer, for example, to a time from the X-ray emission start time point $t_0$ to a fourth time point $t_4$.

The X-ray emitter 200 may emit X-rays toward the object during the X-ray emission time. In an embodiment, the X-ray emission time may be determined according to an imaging protocol (e.g., an APR protocol). In the embodiment illustrated in the second timing chart 400$T_2$ of FIG. 4, the X-ray emitter 200 may emit X-rays toward the object during the time from the X-ray emission start time point $t_0$ to a third time point $t_3$.

The X-ray detector 100 may determine the dynamic window time 430 by adjusting the window time based on the third time point $t_3$ at which the X-ray emission by the X-ray emitter 200 ends. In an embodiment, the X-ray detector 100 may receive an X-ray emission end signal from an automatic exposure control (AEC) device, and obtain information about the third time point $t_3$ at which the X-ray emission ends, based on the received X-ray emission end signal. In an embodiment, the X-ray detector 100 may receive a setting value for the X-ray emission time from the workstation 300 (see FIG. 1), and obtain information about the third time point $t_3$ at which the X-ray emission ends, based on the received setting value for the X-ray emission time. Here, the 'setting value for the X-ray emission time' may be an X-ray emission time determined according to an imaging protocol (e.g., an APR protocol). However, the present disclosure is not limited thereto, and the setting value for the X-ray emission time may be a time determined by the workstation according to an input received from the user.

In an embodiment, the X-ray detector 100 may determine the dynamic window time 430 by determining, as an end time point of the window time, the fourth time point $t_4$ at which a latency 440 has elapsed from the third time point $t_3$ at which the X-ray emission ends. The latency 440 may include a latency due to transmission and reception of the X-ray emission end signal, a remaining X-ray processing time of an X-ray tube, and a time due to afterglow and a potential change of the X-ray detector. In an embodiment, the latency 440 may include at least one of a first latency due to transmission and reception of the X-ray emission end signal between the AEC device and the HVG, a second latency required for the remaining X-rays in the X-ray tube in the HVG to dissipate, a third latency required for afterglow of a scintillator in the X-ray detector 100 to dissipate, and a fourth latency required for electron-hole pairs to be formed inside the PIN diode in the X-ray detector 100 and change the potential.

The X-ray detector 100 obtains X-ray image data about the object by performing a read-out at the fourth time point $t_4$ at which the latency 440 ends. The X-ray detector 100 may perform the read-out during a read-out time 450 from the fourth time point $t_4$.

Because it is difficult to specify the output characteristics of an HVG configured to apply a high voltage to the X-ray emitter 200, an X-ray imaging device using a general X-ray detector 100 performs X-ray imaging using a window time of the X-ray detector 100 that is fixed to a preset value, or using a static window time that is set according to the characteristics of the object (e.g., a patient's age, the type of the object, or the thickness of the object). Referring to the first timing chart 400$T_1$, the X-ray detector 100 receives X-rays during the preset static window time 410 regardless of a time point at which the X-ray emission by the X-ray emitter 200 ends. The static window time 410 may be set differently depending on a patient's age, the type of an object, or the thickness of the object. For example, the static window time 410 may be 550 ms, but is not limited thereto.

In general, the static window time 410 of the X-ray detector 100 is longer than a time during which X-rays are actually emitted. In the first timing chart 400$T_1$, even though the time during which X-rays are actually emitted toward the object by the X-ray emitter 200 ends at the first time point $t_1$ (e.g., for the Chest AP imaging protocol) or at the second time point $t_2$ (e.g., for the pelvis imaging protocol), the static window time 410 of the X-ray detector 100 ends at the k-th time point $t_k$ that is subsequent to the second time point $t_2$, there is an issue that an unnecessary waste of time occurs during an X-ray imaging process, a time point for an X-ray image confirmation is delayed, and the process time increases. In addition, as the window time increases, noise due to a dark current in a photo sensor (e.g., an amorphous-Si-based thin-film transistor (TFT) or a PIN diode) of the X-ray detector 100 increases, and the probability of electrons being trapped in an n-layer of the PIN diode increases, resulting in a decrease in the quality of an X-ray image.

In order to address the issues of noise and deterioration of the quality of an X-ray image caused by a photo sensor as the window time of the X-ray detector 100 is set to be longer than an actual X-ray emission time, the present disclosure provides the X-ray detector 100 for variably adjusting the window time according to a time point at which X-ray emission ends, and an operation method of the X-ray detector 100.

Referring to the second timing chart 400$T_2$, the X-ray detector 100 according to an embodiment of the present disclosure may receive X-rays during the dynamic window time 430 by obtaining information about the third time point $t_3$ at which X-ray emission ends, based on an X-ray emission end signal received from the AEC device or a setting value for the X-ray emission time received from the workstation 300 (see FIG. 1), and adjusting the window time based on the third time point $t_3$. The X-ray detector 100 according to an embodiment of the present disclosure may determine, as the end time point of the dynamic window time 430, the fourth time point $t_4$ at which the latency 440 ends, and perform a read-out at the fourth time point $t_4$. Thus, the X-ray detector 100 of the present disclosure operating according to the second timing chart 400$T_2$ may reduce an unnecessary time consumption due to the static window time 410 and minimize and/or reduce a cycle time for subsequent imaging, compared to a general X-ray detector that operates according to the first timing chart 400$T_1$. In addition, the X-ray detector 100 of the present disclosure may confirm an X-ray image as quickly as possible from the X-ray emission start time point $t_0$. In addition, the X-ray detector 100 of the present disclosure may provide a technical effect of improving the quality of an X-ray image by reducing noise caused by a dark current and minimizing and/or reducing an image lag effect due to electrons trapped in an n-layer of the PIN diode.

Figure 5:
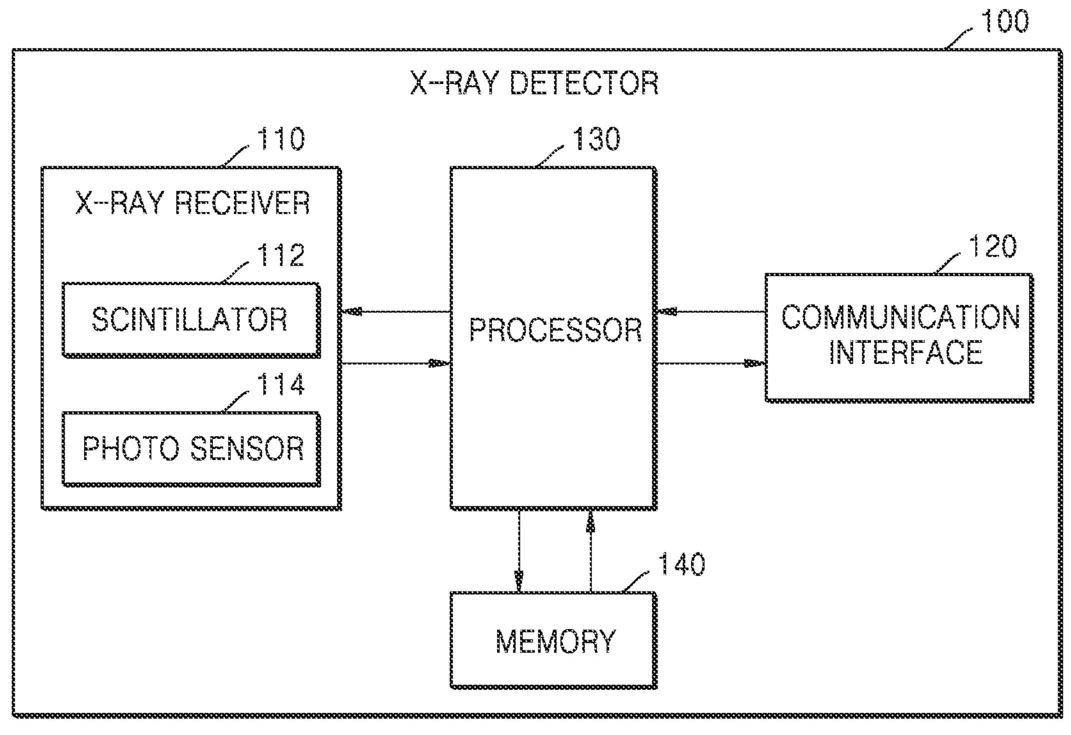
FIG. 5 is a block diagram illustrating an example configuration of an X-ray detector according to various embodiments.

FIG. 5 is a block diagram illustrating an example configuration of the X-ray detector 100 according to various embodiments.

Referring to FIG. 5, the X-ray detector 100 may include an X-ray receiver 110, a communication interface (e.g., including communication circuitry) 120, a processor (e.g., including processing circuitry) 130, and a memory 140. The components illustrated in FIG. 2 are merely examples according to an embodiment of the present disclosure, and the components included in the x-ray detector 100 are not limited to those illustrated in FIG. 5. The X-ray detector 100 may not include some of the components illustrated in FIG. 5, and may further include components not illustrated in FIG. 5. For example, in a case in which the X-ray detector 100 is implemented as a mobile X-ray detector, the X-ray detector 100 may further include a battery.

The X-ray receiver 110 may detect X-rays that have been emitted toward an object by the X-ray emitter 200 (see FIG. 1) (e.g., an X-ray tube) and passed through the object, and generate electric signals corresponding to the intensities of the detected X-rays. The X-ray receiver 110 may include a scintillator 112 and the photo sensor 114.

The scintillator 112 may include various circuitry and is configured to convert X-rays that have passed through the object into visible light. The scintillator 112 may react with X-rays incident on the X-ray detector 100 and thus emit photons having a wavelength in a visible light region (e.g., a wavelength of 300 nm to 800 nm). In an embodiment, in a case in which the X-ray receiver 110 performs direct detection by directly converting X-rays into electric charges, the scintillator 112 may be replaced with a photon-counting detector. The scintillator 112 may include, for example, gadolinium oxysulfide (GoS or Gadox), cesium iodide (CsI), or amorphous silicon (a-Si), but is not limited thereto.

The photo sensor 114 is configured to receive photons emitted by the scintillator 112 and convert the received photons into electric signals. The photo sensor 114 may provide the converted electric signals to the processor 130. The photo sensor 114 may be formed in the form of a substrate on which a plurality of pixels are arranged in a two-dimensional shape of, for example, N×M. The plurality of pixels formed on the substrate of the photo sensor 114 may include a photoelectric convertor configured to generate charges according to visible light and accumulate the generated charges, and a switching element connected to the photoelectric convertor and configured to detect the charges accumulated in the photoelectric convertor. In an embodiment, the photoelectric convertor may include a PIN diode, but is not limited thereto. In an embodiment, the switching element may include a TFT, but is not limited thereto.

In an embodiment, the photo sensor 114 may include an X-ray sensor for detecting the start and end of emission of X-rays by detecting X-rays reaching the X-ray detector 100. The X-ray sensor may include at least one sensor evenly arranged at regular intervals in at least one of the plurality of pixels of the photo sensor 114. The X-ray sensor may be implemented as, for example, a pixel-related AEC or an AEC-related photodiode, but is not limited thereto.

In an embodiment, the X-ray sensor may be short-connected to signal wires without a switching element (e.g., a TFT) arranged between the signal wires, such that signal charges generated by the X-ray sensor may be immediately transferred to the processor 130. When an X-ray is detected, the X-ray sensor may transmit a signal charge to the processor 130 through a signal wire.

The processor 130 may include various processing circuitry. For example, the processor 130 may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions. The processor 130 may for example, be configured to measure a voltage signal on a signal wire connected to the X-ray sensor and monitor the voltage signal in real time. The processor 130 may compare the value of the monitored voltage signal with a preset threshold, and obtain an X-ray emission end signal according to a result of the comparison. In an embodiment, when the value of the voltage signal output from the X-ray sensor is less than the threshold, the processor 130 may recognize that X-ray emission has ended. Through the above-described operation, the X-ray sensor may perform a function of an internal AEC device of the X-ray detector 100. The X-ray sensor will be described in detail below with reference to FIG. 10.

The communication interface 120 may include various communication circuitry and is configured to perform data communication with an external AEC device, the workstation 300 (see FIG. 1), or the controller 400 (see FIG. 1) through a wired or wireless communication network. In an embodiment, the communication interface 120 may receive an X-ray emission end signal from the external AEC device, or receive information about a setting value for the X-ray emission time, under control of the processor 130.

The communication interface 120 may perform data communication with the external AEC device or the workstation 300 using wired data communication, for example, using a communication cable or a wired local area network (LAN). However, the present disclosure is not limited thereto, and in a case in which the X-ray detector 100 is implemented as a wireless detector, the communication interface 120 may perform data communication with the external AEC device or the workstation 300 using at least one of wireless data communication networks according to wireless LAN, Wi-Fi, Bluetooth, Zigbee, Wi-Fi Direct (WFD), Bluetooth Low Energy (BLE), Wireless Broadband Internet (WiBro), Worldwide Interoperability for Microwave Access (WiMAX), Shared Wireless Access Protocol (SWAP), Wireless Gigabit Alliance (WiGig), and radio-frequency (RF) communication.

The processor 130 may generate an X-ray image of an object using electric signals obtained from the X-ray receiver 110. In an embodiment, the processor 130 may include an amplifier circuit configured to amplify an analog signal obtained from the photo sensor 114, and an analog-to-digital (ADC) converter chip configured to convert the amplified analog signal into a digital signal.

The processor 130 may execute program code or one or more instructions stored in the memory 140. The processor 130 may include a hardware component configured to perform arithmetic operations, logic operations, input/output operations, and signal processing. For example, the processor 130 may include at least one of a CPU, a microprocessor, a graphics processing unit, an application-specific integrated circuit (ASIC), a digital signal processor (DSP), a digital signal processing device (DSPD), a programmable logic device (PLD), and a field-programmable gate array (FPGA), but is not limited thereto.

In FIG. 5, the processor 130 is illustrated as one element, but is not limited thereto. In an embodiment, one or more processors 130 may be provided.

The memory 140 may include, for example, at least one of a flash memory-type storage medium, a hard disk-type storage medium, a multimedia card micro-type storage medium, a card-type memory (e.g., secure digital (SD) or extreme digital (XD) memory), random-access memory (RAM), static RAM (SRAM), read-only memory (ROM), electrically erasable programmable ROM (EEPROM), programmable ROM (PROM), a magnetic memory, a magnetic disc, or an optical disc.

The memory 140 may store instructions or program code for performing a function or operation of the X-ray detector 100. In an embodiment, the memory 140 may store at least one of instructions, an algorithm, a data structure, program code, or an application program that is readable by the processor 130. The instructions, the algorithm, the data structure, and the program code stored in the memory 140 may be implemented in a programming or scripting language, for example, C, C++, Java, or an assembler.

In the following example embodiments, the processor 130 may execute instructions or program code of a program stored in the memory 140.

The processor 130 may receive an X-ray emission end signal from an external AEC device through the communication interface 120. In an embodiment, the external AEC device may be an ion chamber-based AEC device. The ion chamber-based AEC device is an AEC configured to, when X-rays are incident into an ion chamber, apply an electric field to an electrode to collect, in the electrode, positive ions and negative ions generated by gas molecules inside the ion chamber and detect a current. When the current value of the detected current is greater than a preset threshold, the ion chamber-based AEC device may transmit an X-ray emission end signal to the X-ray detector to instruct to end X-ray emission.

However, the present disclosure is not limited thereto, and the external AEC device may be implemented as a photocell-based AEC capable of detecting X-rays, such as a photodiode.

The processor 130 may receive information about a setting value for the X-ray emission time, from the workstation 300 through the communication interface 120. In an embodiment, the setting value for the X-ray emission time may be an X-ray emission time determined according to an imaging protocol (e.g., an APR protocol). For example, in a case of a chest AP protocol for imaging a patient's chest, the X-ray emission time may be 10 ms, and in a case of the pelvis protocol for imaging a patient's pelvis, the X-ray emission time may be 100 ms. However, the present disclosure is not limited thereto. In an embodiment, the setting value for the X-ray emission time may be a time determined by the workstation 300 according to an input received from the user.

In an embodiment, the processor 130 may obtain an X-ray emission end signal from the X-ray sensor included in the photo sensor 114. As described above regarding the X-ray sensor, the processor 130 may monitor the value of a voltage signal output from the X-ray sensor, and when the value of the voltage signal is less than a preset threshold in a result of the monitoring, recognize that X-ray emission has ended.

The processor 130 may adjust the window time of the X-ray detector 100 based on the X-ray emission end signal obtained from the external AEC device and the X-ray sensor, or the setting value for the X-ray emission time received from the workstation 300. The 'window time' refers to a time for the X-ray detector to receive X-rays that have passed through the object.

The processor 130 may variably adjust the window time of the X-ray detector 100 based on a time point at which the X-ray emission end signal is received. In an embodiment, the processor 130 may adjust the window time by determining, as the start time point of the window time, a time point at which X-ray emission is started, and determining, as the end time point of the window time, a time point at which the X-ray emission end signal is received. In an embodiment, the processor 130 may determine, as the end time point of the window time, a time point at which a predetermined latency has elapsed from the time point at which the X-ray emission end signal is received. The latency may include a latency due to transmission and reception of the X-ray emission end signal, a remaining X-ray processing time of an X-ray tube, and a time due to afterglow and a potential change of the X-ray detector 100. In an embodiment, the latency may include at least one of a first latency due to transmission and reception of the X-ray emission end signal between the external AEC device and the HVG, a second latency required for the remaining X-rays in the X-ray tube in the HVG to dissipate, a third latency required for afterglow of the scintillator 112 to dissipate, and a fourth latency required for electron-hole pairs to be formed inside a PIN diode included in the photo sensor 114 and change the potential. The first to fourth latencies will be described in detail below with reference to a timing chart 800T illustrated in FIG. 8.

When the window time ends, the processor 130 may obtain X-ray image data by performing a read-out. When the processor 130 recognizes that the window time has elapsed, the processor 130 may obtain X-ray image data by releasing charges accumulated in the PIN diode in the photo sensor 114, reading out the released charges, and converting the charges into image data. The readout operation of the X-ray detector 100 is widely known to those of skill in the art, and thus, detailed descriptions thereof will be omitted.

Figure 6:
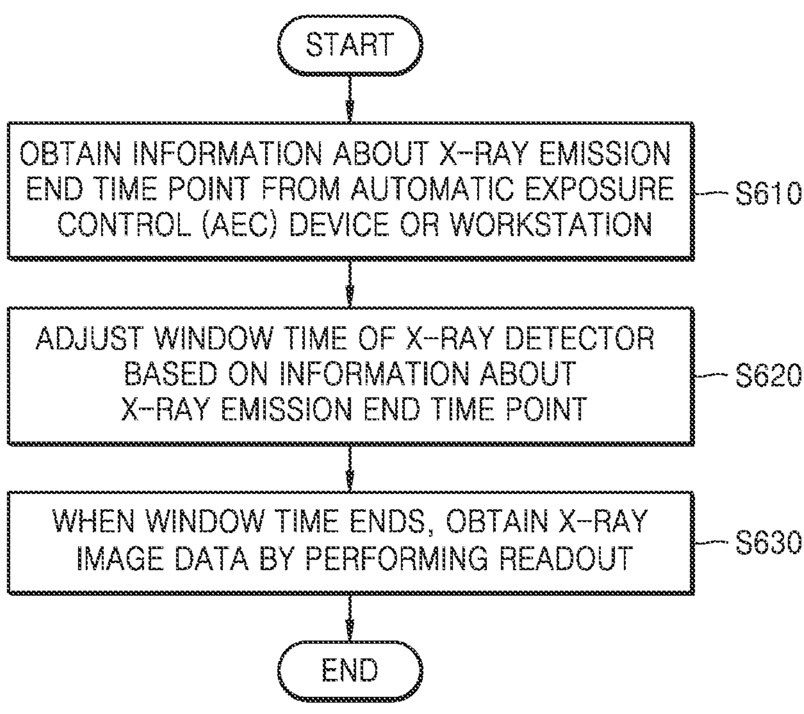
FIG. 6 is a flowchart illustrating an example operation of an X-ray detector according to various embodiments.

FIG. 6 is a flowchart illustrating an example operation of the X-ray detector 100 according to various embodiments.

In operation S610, the X-ray detector 100 obtains information about an X-ray emission end time point, from an AEC device or the workstation 300 (see FIG. 1). In an embodiment, the X-ray detector 100 may receive an X-ray emission end signal from an ion chamber-based AEC device or a photocell-based AEC device, and obtain information about the X-ray emission end time point based on the received X-ray emission end signal. In an embodiment, the X-ray detector 100 may recognize the end of X-ray emission using the X-ray sensor included in the internal photo sensor 114 (see FIG. 5), and obtain the information about the X-ray emission end time point, from a time point of the recognizing. The X-ray sensor may be, for example, a pixel-related AEC or an AEC-related photodiode, but is not limited thereto.

In an embodiment, the X-ray detector 100 may receive a setting value for the X-ray emission time from the workstation 300, and obtain information about the X-ray emission end time point based on the received setting value for the X-ray emission time. In an embodiment, the 'setting value for the X-ray emission time' may be an X-ray emission time determined according to an imaging protocol (e.g., an APR protocol). For example, in a case of a chest AP protocol for imaging a patient's chest, the X-ray emission time may be 10 ms, and in a case of the pelvis protocol for imaging a patient's pelvis, the X-ray emission time may be 100 ms. In an embodiment, the setting value for the X-ray emission time may be a time determined by the workstation 300 according to an input received from the user.

In operation S620, the X-ray detector 100 adjusts the window time of the X-ray detector 100 based on the information about the X-ray emission end time point. The 'window time' refers to a time for the X-ray detector to receive X-rays that have passed through an object.

In an embodiment, the X-ray detector 100 may variably adjust the window time by determining, as the start time point of the window time, a time point at which X-ray emission is started, and determining, as the end time point of the window time, a time point at which the X-ray emission end signal is received. In an embodiment, the X-ray detector 100 may determine, as the end time point of the window time, a time point at which a predetermined latency has elapsed from the time point at which the X-ray emission end signal is received. The latency may include a latency due to transmission and reception of the X-ray emission end signal, a remaining X-ray processing time of an X-ray tube, and a time due to afterglow and a potential change of the X-ray detector 100. In an embodiment, the latency may include at least one of a first latency due to transmission and reception of the X-ray emission end signal between the external AEC device and the HVG, a second latency required for the remaining X-rays in the X-ray tube in the HVG to dissipate, a third latency required for afterglow of the scintillator 112 to dissipate, and a fourth latency required for electron-hole pairs to be formed inside a PIN diode included in the photo sensor 114 and change the potential.

In operation S630, when the window time ends, the X-ray detector 100 obtains X-ray image data by performing a read-out. In an embodiment, when the X-ray detector 100 recognizes that the window time has elapsed, the X-ray detector 100 may obtain X-ray image data by releasing charges accumulated in the PIN diode in the photo sensor 114 (see FIG. 5), reading out the released charges, and converting the charges into image data.

Figure 7:
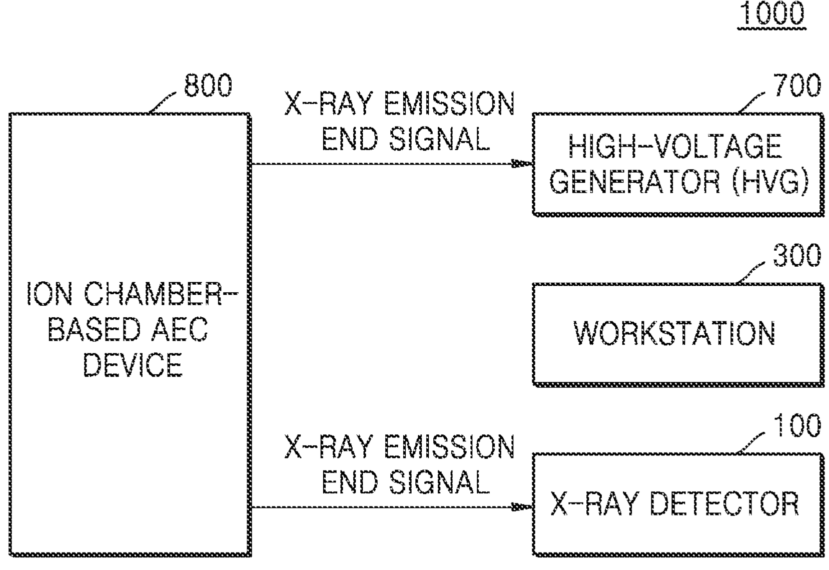
FIG. 7 is a diagram illustrating an example signal flow between components of an X-ray imaging device, according to various embodiments.

FIG. 7 is a diagram illustrating an example signal flow between components of the X-ray imaging device 1000, according to various embodiments.

Referring to FIG. 7, the X-ray imaging device 1000 may include the X-ray detector 100, the workstation 300, an HVG 700, and an ion chamber-based AEC device 800. FIG. 7 simply illustrates components for describing transmission and reception of X-ray emission end signals between the components of the X-ray imaging device 1000, and the components of X-ray imaging device 1000 are not limited to those illustrated in FIG. 7.

The HVG 700 generates a high voltage for generating X-rays and applies the high voltage to the X-ray emitter 200 (see FIG. 1). The HVG 700 may generate a tube voltage or a tube current according to imaging conditions or a imaging protocol input by the workstation 300 or the controller 400 (see FIG. 1), and apply the tube voltage or tube current to the X-ray source of the X-ray emitter 200. In an embodiment, the HVG 700 may apply a high voltage to the X-ray source during an X-ray emission time determined according to an imaging protocol (e.g., an APR protocol). In an embodiment, the HVG 700 may apply a high voltage to the X-ray source during an X-ray emission time determined through a user input.

The ion chamber-based AEC device 800 may include a gas-filled X-ray detection device, and is also referred to as an ionization box or an ionization bath. In an embodiment, the ion chamber-based AEC device 800 includes a high-voltage electrode, a signal electrode, and an insulator, and a high voltage is applied between the high-voltage electrode and the signal electrode by a power source. When X-rays from the X-ray source are emitted toward one surface inside a case of the ion chamber-based AEC device 800, gas in the case is ionized to form an ion pair, and an electric field is formed between the high-voltage electrode and the signal electrode by the power source, causing electrons in the ion pair to drift toward the signal electrode and ionized molecules to drift toward the high-voltage electrode. A current is generated by the drift of the electrons and the ionized molecules, and the ion chamber-based AEC device 800 may measure the amount of X-rays by detecting the generated current. When the detected current value is greater than a preset threshold, the ion chamber-based AEC device 800 may end X-ray emission and transmit an X-ray emission end signal to the HVG 700.

In an embodiment, the ion chamber-based AEC device 800 may transmit an X-ray emission end signal to the X-ray detector 100.

The X-ray detector 100 may variably adjust the window time based on the X-ray emission end signal received from the ion chamber-based AEC device 800. In an embodiment, the processor 130 of the X-ray detector 100 may determine, as the end point of the exposure time, a time point at which a predetermined latency has elapsed from a time point at which the X-ray emission end signal is received from the ion chamber-based AEC device 800. The latency may include a latency required for the X-ray emission end signal to be transmitted from the ion chamber-based AEC device 800 to the HVG 700, a time for processing the remaining X-rays of the X-ray tube, and a time due to afterglow and a potential change of the X-ray detector 100. The latency will be described in detail below with reference to the timing chart 800T illustrated in FIG. 8.

Figure 8:
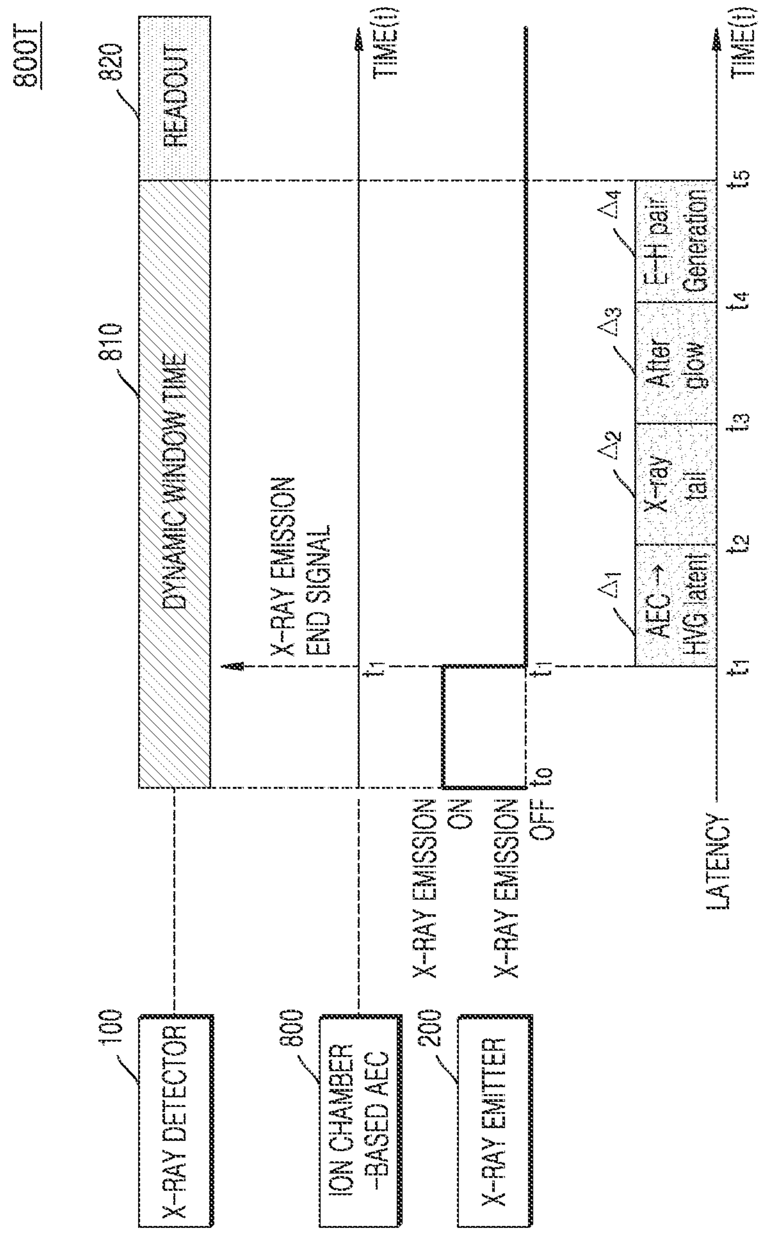
FIG. 8 is a diagram illustrating an example timing chart illustrating a window time adjusted by an X-ray detector, according to various embodiments.

FIG. 8 is a diagram illustrating an example timing chart 800T illustrating a window time 810 adjusted by the X-ray detector 100, according to various embodiments.

Referring to the timing chart 800T illustrated in FIG. 8, the X-ray detector 100 may determine, as the window time 810, a time from an X-ray emission start time point $t_0$ at which X-ray emission is started by the X-ray emitter 200, to a fifth time point $t_5$ at which a first latency Δ1 to a fourth latency Δ4 have elapsed after the X-ray emission ends. In an embodiment, the processor 130 (see FIG. 5) of the X-ray detector 100 may determine, as the end time point of the window time 810, the fifth time point $t_5$ at which the first latency Δ1 to the fourth latency Δ4 have elapsed from the first time point $t_2$ at which the X-ray emission end signal is received from the ion chamber-based AEC device 800.

The first latency Δ1 may refer, for example, to a time required for the X-ray emission end signal to be transmitted from the ion chamber-based AEC device 800 to the HVG 700 (see FIG. 7). The X-ray detector 100 may receive the X-ray emission end signal from the ion chamber-based AEC device 800 at the first time point $t_1$, whereas the HVG 700 may not receive the X-ray emission end signal from the ion chamber-based AEC device 800, but may receive the X-ray emission end signal at a second time point $t_2$ at which the first latency Δ1 has elapsed. In this case, the X-ray detector 100 receives the X-ray emission end signal from the HVG 700 and needs to wait until the second time point $t_2$ for blocking a high voltage applied to the X-ray source of the X-ray emitter 200 (see FIG. 1).

The first latency Δ1 may vary depending on a communication connection method or a communication connection standard between the HVG 700 and the ion chamber-based AEC device 800. In an embodiment, the first latency Δ1 may be determined according to whether the HVG 700 and the ion chamber-based AEC device 800 are connected to each other through wired or wireless communication, or, when they are connected to each other through wired communication, according to the communication standard used for connecting them through a cable for enabling data transmission. The processor 130 may obtain information about the first latency Δ1 based on information about the communication method or the communication connection standard between the HVG 700 and the ion chamber-based AEC device 800.

The second latency Δ2 may refer, for example, to a time required for all remaining X-rays (X-ray tails) to dissipate after X-rays are cut off by the HVG 700. In the embodiment illustrated in FIG. 8, the second latency Δ2 may be a time from the second time point $t_2$ to the third time point $t_3$. The second latency Δ2 may be determined according to specification information or state information of the X-ray tube or the HVG 700. The processor 130 may obtain information about the second latency Δ2 based on at least one of the specification information and the state information of the X-ray tube or the HVG 700. In an embodiment, the processor 130 may increase the second latency Δ2 in proportion to the degree of wearing away of the HVG 700.

The third latency Δ3 may refer, for example, to a time required for afterglow to dissipate from the scintillator 112 (see FIG. 5) in the X-ray receiver 110 (see FIG. 5) of the X-ray detector 100. In the embodiment illustrated in FIG. 8, the third latency Δ3 may be a time from the third time point $t_3$ to the fourth time point $t_4$. The third latency Δ3 may vary depending on a material included in the scintillator 112 (e.g., Gadox, CsI, or a-Si). The processor 130 may obtain information about the third latency Δ3 based on information about the material included in the scintillator 112.

The fourth latency Δ4 may refer, for example, to a time required for an electron-hole pair to be formed inside a PIN diode among the components of the photo sensor 114 (see FIG. 5) in the X-ray receiver 110 and to change a source potential of a TFT. In the embodiment illustrated in FIG. 8, the fourth latency Δ4 may be a time from the fourth time point $t_4$ to the fifth time point $t_5$.

The fourth latency Δ4 may vary depending on the thickness of the PIN diode and the value of a voltage applied to the PIN diode. The processor 130 may obtain information about the fourth latency Δ4 based on information about the thickness of the PIN diode included in the photo sensor 114 and information about the voltage applied to the PIN diode.

The processor 130 of the X-ray detector 100 may perform a read-out during a readout time 820 from the fifth time point $t_5$ at which the window time 810 ends.

Figure 9A:
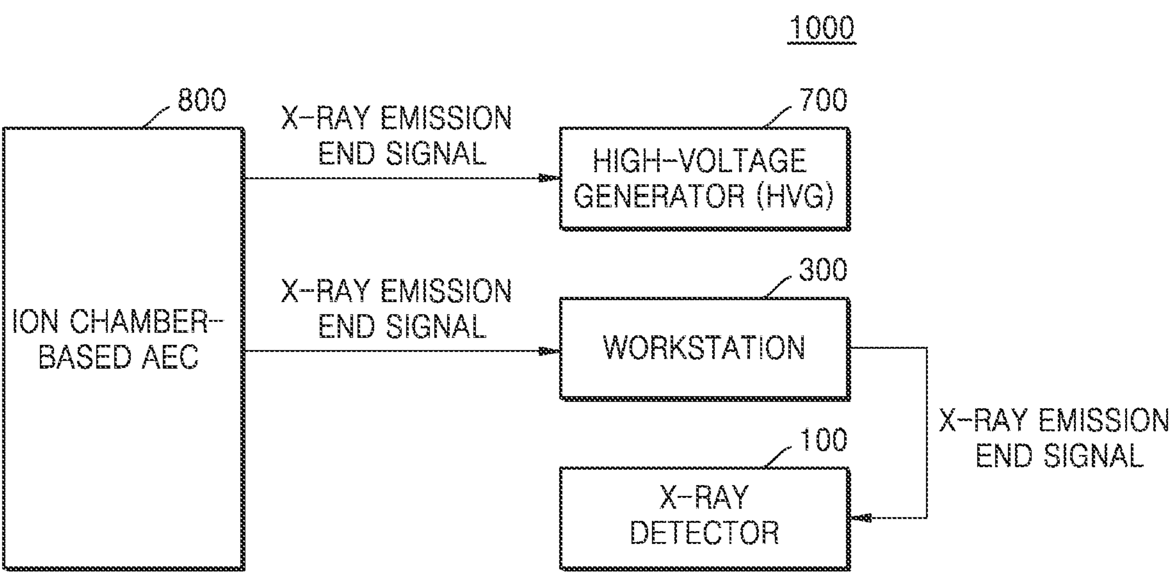
FIG. 9A is a diagram illustrating an example signal flow between components of an X-ray imaging device, according to various embodiments.

FIG. 9A is a diagram illustrating an example signal flow between components of the X-ray imaging device 1000, according to various embodiments.

Referring to FIG. 9A, the X-ray imaging device 1000 may include the X-ray detector 100, the workstation 300, the HVG 700, and the ion chamber-based AEC device 800. FIG. 9A illustrates only components for describing transmission and reception of X-ray emission end signals between the components of the X-ray imaging device 1000, and the components of X-ray imaging device 1000 are not limited to those illustrated in FIG. 9A. The HVG 700 and the ion chamber-based AEC device 800 are the same as or similar to the HVG 700 and the ion chamber-based AEC device 800 both illustrated in FIG. 7, and thus, redundant descriptions thereof may not be repeated here.

The ion chamber-based AEC device 800 may transmit an X-ray emission end signal to the HVG 700 and the workstation 300.

The workstation 300 is a device configured to receive a user input for selecting a setting value or an imaging protocol related to X-ray imaging, and display an X-ray image obtained through X-ray imaging. In an embodiment, the workstation 300 may be configured as a console PC, but is not limited thereto. The workstation 300 may be connected to the X-ray detector 100 through a wired or wireless communication network. The workstation 300 may be connected to the X-ray detector 100 through, for example, a high-speed digital interface such as low-voltage differential signaling (LVDS), an asynchronous serial communication such as universal asynchronous receiver-transmitter (UART), or a low-latency network protocol such as error synchronous serial communication or controller area network (CAN), but is not limited thereto.

The workstation 300 may transmit, to the X-ray detector 100, the X-ray emission end signal received from the ion chamber-based AEC device 800.

The X-ray detector 100 may receive the X-ray emission end signal from the workstation 300 through the communication interface 120 (see FIG. 5). The processor 130 (see FIG. 5) of the X-ray detector 100 may adjust the window time of the X-ray detector 100 based on a time point of receiving the X-ray emission end signal, and a predetermined latency. A detailed embodiment in which the processor 130 adjusts the window time of the X-ray detector 100 will be described in detail below with reference to a timing chart 1100T of FIG. 11.

Figure 9B:
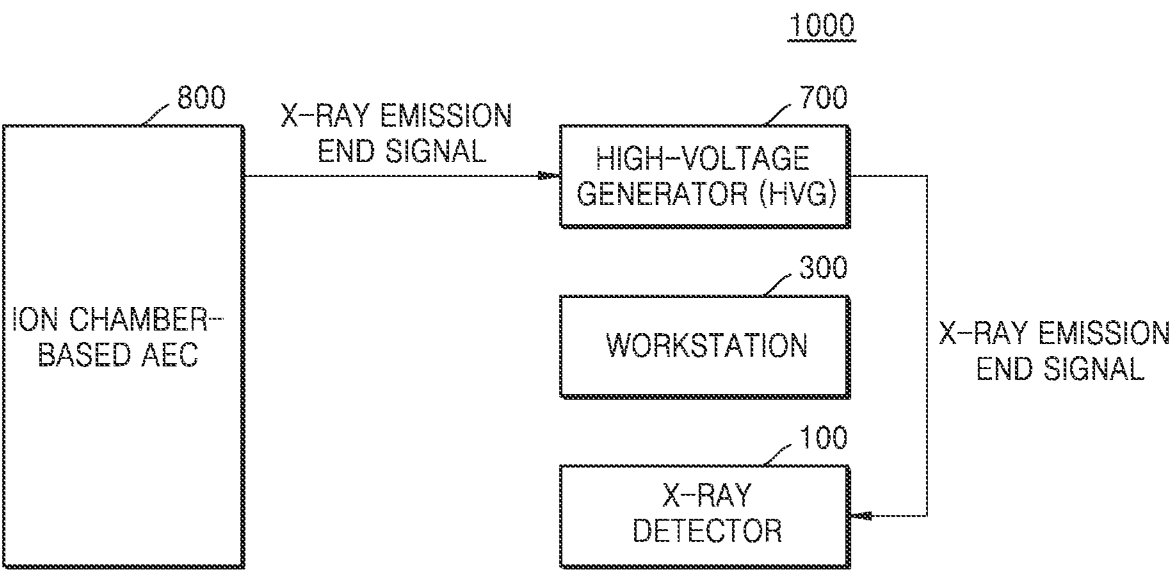
FIG. 9B is a diagram illustrating an example signal flow between components of an X-ray imaging device, according to various embodiments.

FIG. 9B is a diagram illustrating an example signal flow between components of the X-ray imaging device 1000, according to various embodiments.

Referring to FIG. 9B, the X-ray imaging device 1000 may include the X-ray detector 100, the workstation 300, the HVG 700, and the ion chamber-based AEC device 800. The embodiment illustrated in FIG. 9B is the same as or similar to the embodiment of FIG. 9A except that the HVG 700, instead of the workstation 300, transmits an X-ray emission end signal to the X-ray detector 100, and thus, redundant descriptions thereof may not be repeated here.

The ion chamber-based AEC device 800 may transmit an X-ray emission end signal to the HVG 700. The first latency Δ1 (see FIG. 8) may be required for completion of transmission of the X-ray emission end signal from the ion chamber-based AEC device 800 to the HVG 700.

As the HVG 700 receives the X-ray emission end signal from the ion chamber-based AEC device 800, the HVG 700 may block a high voltage applied to the X-ray source of the X-ray emitter 200 (see FIG. 1). The HVG 700 may transmit an X-ray emission end signal to the X-ray detector 100.

The X-ray detector 100 may receive the X-ray emission end signal from the HVG 700 through the communication interface 120 (see FIG. 5). The processor 130 (see FIG. 5) of the X-ray detector 100 may adjust the window time of the X-ray detector 100 based on a time point of receiving the X-ray emission end signal from the HVG 700, and a predetermined latency. A detailed embodiment in which the processor 130 adjusts the window time of the X-ray detector 100 will be described in detail below with reference to the timing chart 1100T of FIG. 11.

Figure 10:
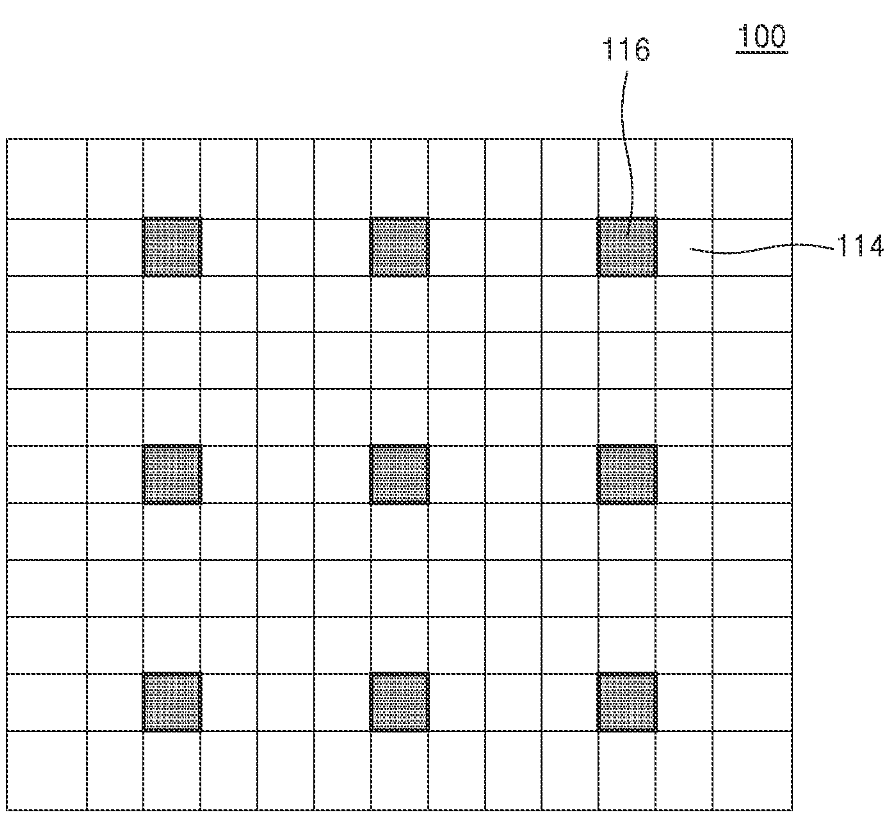
FIG. 10 is a diagram illustrating a plan view of an X-ray detector according to various embodiments.

FIG. 10 is a diagram illustrating a plan view of the X-ray detector 100 according to various embodiments.

Referring to FIG. 10, the X-ray detector 100 may include the photo sensor 114 and an X-ray sensor 116. FIG. 10 merely illustrates various components for describing an operation of detecting X-rays emitted to the X-ray detector 100 using the X-ray sensor 116, and the components of the X-ray detector 100 are not limited to those illustrated in FIG. 10.

The photo sensor 114 is configured to receive photons emitted by the scintillator 112 (see FIG. 5) and convert them into electric signals. The photo sensor 114 may be formed in the form of a substrate on which a plurality of pixels are arranged in a two-dimensional shape of, for example, N×M. The photo sensor 114 is the same as or similar to the photo sensor 114 illustrated in FIG. 5, and thus redundant descriptions thereof may not be repeated here.

The X-ray sensor 116 may be arranged adjacent to at least one of the photo sensors 114 configured as a plurality of pixels. The X-ray sensor 116 may not be arranged biased toward a particular area, but may be arranged at a certain distance from an imaging area. In an embodiment, the X-ray sensor 116 may arranged at a position where at least one photo sensor 114 is arranged to replace the at least one photo sensor 114.

The X-ray sensor 116 may detect X-rays reaching the X-ray detector 100. In an embodiment, the X-ray sensor 116 may detect visible light converted from X-rays by the scintillator 112, convert the visible light into electric signals, and output a voltage value according to the conversion. The X-ray sensor 116 may be implemented as, for example, a pixel-related AEC or an AEC-related photodiode, but is not limited thereto.

The processor 130 may obtain information about the end of X-ray emission, from the X-ray sensor 116. In an embodiment, unlike the photo sensor 114, the X-ray sensor 116 may be short-connected to signal wires without a switching element (e.g., a TFT) arranged between the signal wires, and thus, signal charges generated by the X-ray sensor 116 may be immediately transferred to the processor 130 (see FIG. 5). A voltage value output by the X-ray sensor 116 may be transmitted to the processor 130 through a signal wire. The processor 130 may measure the voltage value on the signal wire connected to the X-ray sensor 116 and monitor the voltage value in real time. The processor 130 may obtain an X-ray emission end signal from the X-ray sensor 116. In an embodiment, when the voltage value output from the X-ray sensor 116 is less than a preset threshold, the processor 130 may recognize that X-ray emission has ended.

The processor 130 may determine, as an X-ray emission end time point, a time point at which the voltage value received from the X-ray sensor 116 is identified as being less than the preset threshold. In an embodiment, the processor 130 may adjust the window time of the X-ray detector 100 based on the time point determined as the X-ray emission end time point, and a predetermined latency. A detailed embodiment in which the processor 130 adjusts the window time of the X-ray detector 100 will be described in greater detail below with reference to the timing chart 1100T of FIG. 11.

Figure 11:
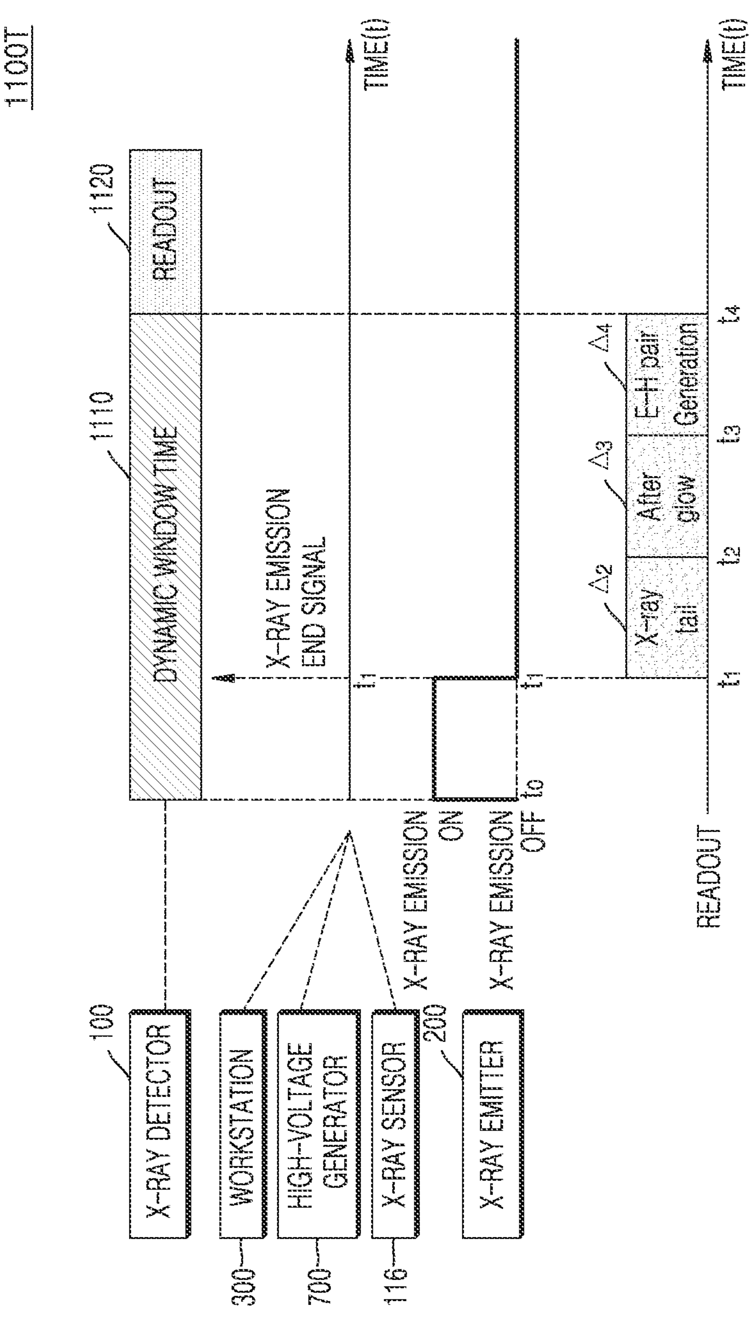
FIG. 11 is a diagram illustrating an example timing chart illustrating a window time adjusted by an X-ray detector, according to various embodiments.

FIG. 11 is a diagram illustrating an example timing chart 1100T illustrating a window time 1110 adjusted by the X-ray detector 100, according to various embodiments.

Referring to the timing chart 1100T illustrated in FIG. 11, the X-ray detector 100 may determine, as the window time 1110, a time from an X-ray emission start time point $t_0$ at which X-ray emission is started by the X-ray emitter 200, to a fourth time point $t_5$ at which a second latency ≢2 to a fourth latency Δ4 have elapsed after the X-ray emission ends.

In an embodiment, the X-ray detector 100 may receive an X-ray emission end signal from any one of the workstation 300, the HVG 700, and the X-ray sensor 116. An embodiment in which the X-ray detector 100 receives an X-ray emission end signal from the workstation 300 is the same as or similar to that described above with reference to FIG. 9A, and an embodiment in which the X-ray detector 100 receives an X-ray emission end signal from the HVG 700 is the same as or similar to that described above with reference to FIG. 9B. In addition, an embodiment in which the X-ray detector 100 obtains information about the end of X-ray emission by monitoring a voltage value output by the X-ray sensor 116 is the same as or similar to that described above with reference to FIG. 10. Thus, the descriptions provided above with reference to FIGS. 9A, 9B, and 10 may not be repeated here.

The processor 130 (see FIG. 5) of the X-ray detector 100 may determine, as the end time point of the window time 1110, the fourth time point $t_4$ at which the second delay time Δ2 to the fourth latency Δ4 have elapsed from the first time point $t_1$ at which the X-ray emission end signal is received.

The second latency Δ2 may refer, for example, to a time required for all remaining X-rays (X-ray tails) to dissipate after X-rays are cut off by the HVG 700. In the embodiment illustrated in FIG. 11, the second latency Δ2 may be a time from the first time point $t_1$ to the second time point $t_2$.

The third latency Δ3 may refer, for example, to a time required for afterglow to dissipate from the scintillator 112 (see FIG. 5) in the X-ray receiver 110 (see FIG. 5) of the X-ray detector 100. In the embodiment illustrated in FIG. 11, the third latency Δ3 may be a time from the second time point $t_2$ to the third time point $t_3$.

The fourth latency Δ4 may refer, for example, to a time required for an electron-hole pair to be formed inside a PIN diode among the components of the photo sensor 114 (see FIG. 5) in the X-ray receiver 110 and to change a source potential of a TFT. In the embodiment illustrated in FIG. 11, the fourth latency Δ4 may be a time from the third time point $t_3$ to the fourth time point $t_4$.

Detailed descriptions of each of the second latency Δ2 to the fourth latency Δ4 and a method, performed by the processor 130, of obtaining information about the second latency Δ2 to the fourth latency Δ4 are the same as or similar to those provided above with reference to FIG. 8, and thus, redundant descriptions may not be repeated here.

The processor 130 of the X-ray detector 100 may perform a read-out during a readout time 1120 from the fourth time point $t_4$ at which the window time 1110 ends.

The X-ray detector 100 according to the timing chart 1100T illustrated in FIG. 11 may not include the first latency Δ1, and may adjust the window time 1110 such that the window time 1110 ends at a time point at which the second latency Δ2 to the fourth latency Δ4 have elapsed from a time point at which the X-ray emission end signal is received. This is because the X-ray detector 100 according to the timing chart 1100T of FIG. 11 receives an X-ray emission end signal from the workstation 300 or the HVG 700, or obtains, from the X-ray sensor 116 in the X-ray detector 100, information about the X-ray emission end time point, and thus, there is no need to consider the first latency Δ1 required for the X-ray emission end signal to be transmitted from an external AEC device (e.g., the ion chamber-based AEC device 800 (see FIG. 7)) to the HVG 700. When the X-ray detector 100 receives an X-ray emission end signal from the workstation 300 or the HVG 700, or obtains information about an X-ray emission end time point from the X-ray sensor 116 in the X-ray detector 100, the X-ray detector 100 can adjust the window time 1110 to be shorter than that when receiving an X-ray emission end signal directly from an external AEC device (see FIGS. 7 and 8). Thus, the X-ray detector 100 operating according to the timing chart 1100T illustrated in FIG. 11 may minimize and/or reduce a cycle time for subsequent imaging, and confirming an X-ray image more quickly as compared to conventional imaging.

Figure 12:
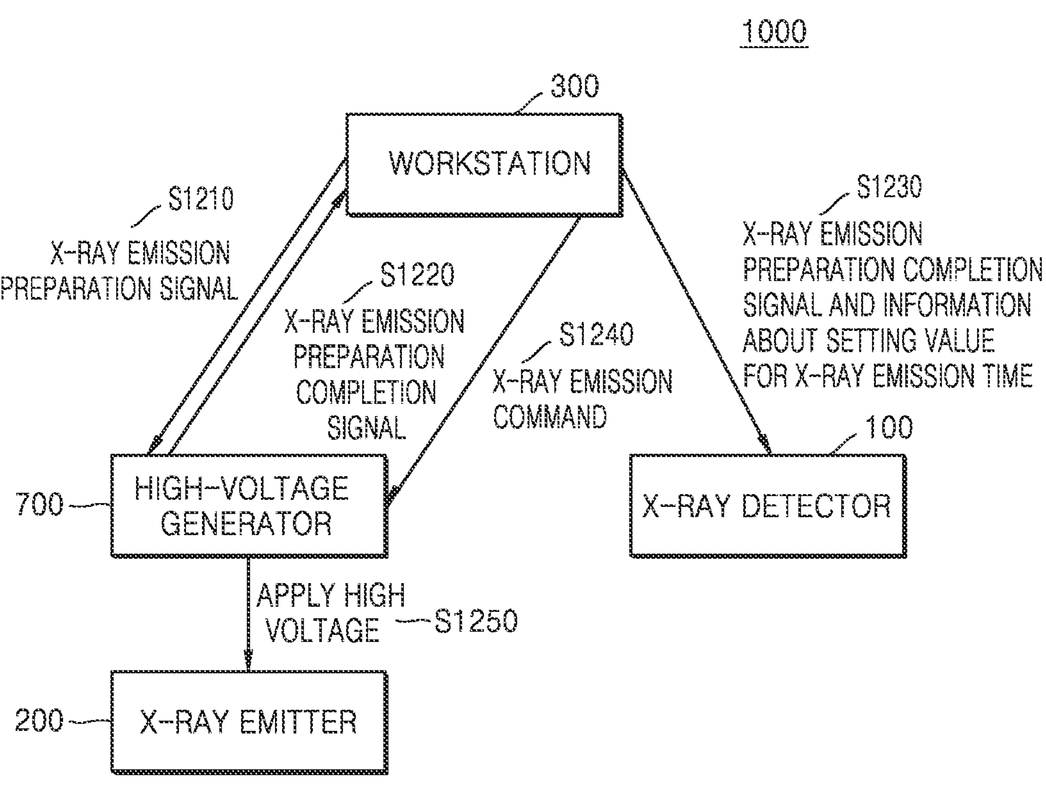
FIG. 12 is a diagram illustrating an example signal flow between components of an X-ray imaging device, according to various embodiments.

FIG. 12 is a diagram illustrating an example signal flow between components of the X-ray imaging device 1000, according to various embodiments.

Referring to FIG. 12, the X-ray imaging device 1000 may include the X-ray detector 100, the X-ray emitter 200, the workstation 300, and the HVG 700. FIG. 12 illustrates only components for describing transmission and reception of signals between the components of the X-ray imaging device 1000, and the components of X-ray imaging device 1000 are not limited to those illustrated in FIG. 12.

In operation S1210, the workstation 300 transmits an X-ray emission preparation signal to the HVG 700.

As the HVG 700 receives the X-ray emission preparation signal from the workstation 300, the HVG 700 may generate a high voltage to prepare to apply a high voltage to the X-ray emitter 200. In operation S1220, when the HVG 700 has generated the high voltage and prepared to apply the high voltage, the HVG 700 may transmit an X-ray emission preparation completion signal to the workstation 300.

In operation S1230, as the workstation 300 receives the X-ray emission preparation completion signal from the HVG 700, the workstation 300 may transmit an X-ray emission preparation completion signal to the X-ray detector 100. The X-ray detector 100 may receive the X-ray emission preparation completion signal from the workstation 300 through the communication interface 120 (see FIG. 5). The processor 130 (see FIG. 5) of the X-ray detector 100 may determine, as the start time point of the window time of the X-ray detector 100, a time point at which the X-ray emission preparation completion signal is received from the workstation 300. As the X-ray emission preparation completion signal is received, the processor 130 may control the X-ray receiver 110 (see FIG. 5) to receive X-rays.

In an embodiment, the workstation 300 may transmit, to the X-ray detector 100, information about a setting value for the X-ray emission time, along with the X-ray emission preparation completion signal. In an embodiment, the 'setting value for the X-ray emission time' may be an X-ray emission time determined according to an imaging protocol (e.g., an APR protocol). For example, in a case of a chest AP protocol for imaging a patient's chest, the X-ray emission time may be 10 ms, and in a case of the pelvis protocol for imaging a patient's pelvis, the X-ray emission time may be 100 ms. In an embodiment, the setting value for the X-ray emission time may be a time determined by the workstation 300 according to an input received from the user.

The processor 130 of the X-ray detector 100 may identify a time point at which the X-ray emission time ends, based on the setting value for X-ray emission time. The processor 130 may adjust the window time based on the end time point of the X-ray emission time, and a predetermined latency. In an embodiment, the processor 130 may determine, as the end time point of the window time, a time point at which the predetermined latency has elapsed from the end time point of the X-ray emission time. A detailed embodiment in which the processor 130 adjusts the window time of the X-ray detector 100 will be described in greater detail below with reference to a timing chart 1300T of FIG. 13.

In operation S1240, the workstation 300 transmits an X-ray emission command to the HVG 700.

In operation S1250, the HVG 700 applies a high voltage to the X-ray emitter 200 according to the X-ray emission command received from the workstation 300.

When the X-ray emission command is transmitted from the workstation 300 to the HVG 700 and the high voltage is applied to the X-ray emitter 200 by the HVG 700, a latency may occur due to signal transmission and reception. The latency due to signal transmission and reception between the workstation 300, the HVG 700, and the X-ray emitter 200 will be described in greater detail below with reference to FIG. 13.

Figure 13:
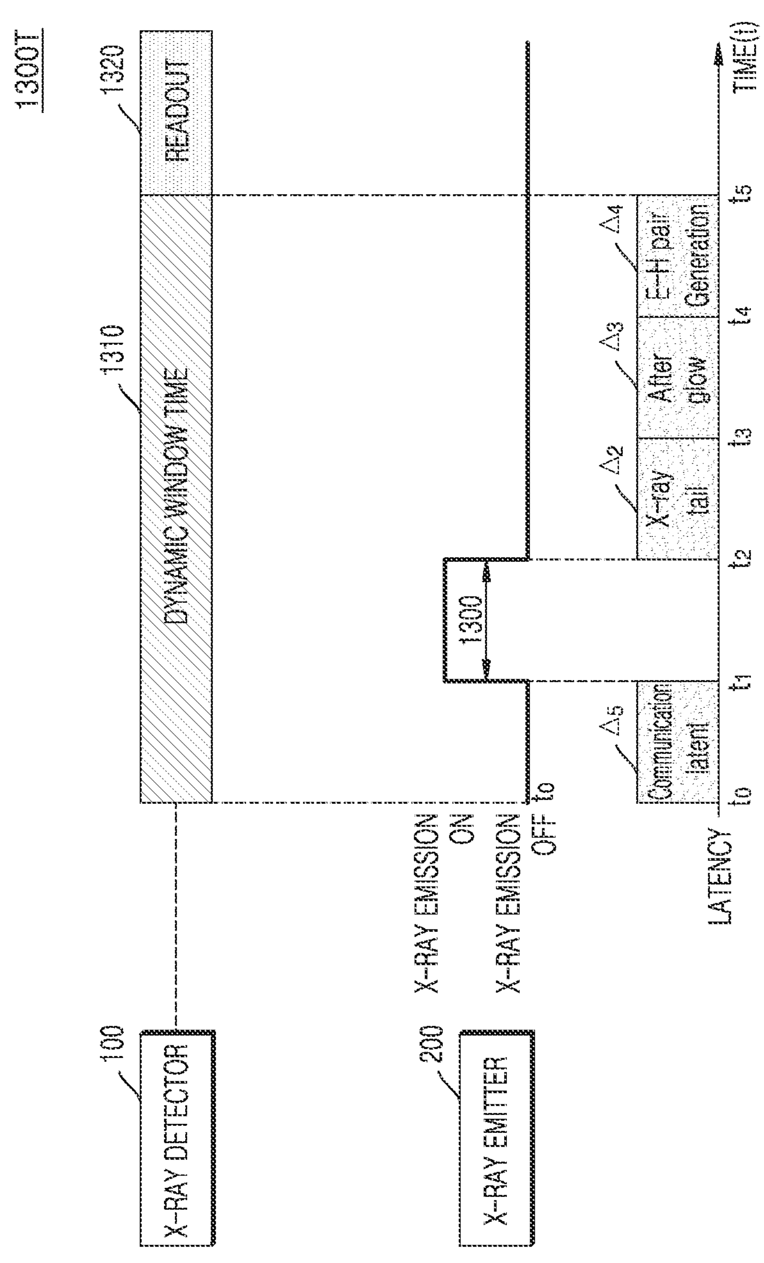
FIG. 13 is a diagram illustrating an example timing chart illustrating a window time adjusted by an X-ray detector, according to various embodiments.

FIG. 13 is a diagram illustrating an example timing chart illustrating a window time 1310 adjusted by the X-ray detector 100, according to various embodiments.

Referring to the timing chart 1300T illustrated in FIG. 13, the X-ray detector 100 may determine, as the window time 1310, a time from a time point $t_0$ at which an X-ray emission preparation completion signal is received from the workstation 300 (see FIG. 12), to a fourth time point $t_4$ at which a second latency Δ2 to a fourth latency Δ4 have elapsed after X-ray emission is ended by the X-ray emitter 200.

The X-ray emitter 200 may receive a high voltage applied from the HVG 700 (see FIG. 12), and emit X-rays toward an object at the first time point $t_1$. A fifth latency Δ5 may refer, for example, to a time required for signal transmission and reception between the workstation 300, the HVG 700, and the X-ray emitter 200 from the time point $t_0$ at which the X-ray detector 100 receives the X-ray emission preparation completion signal from the workstation 300. In an embodiment, the fifth latency Δ5 may include a time required for an X-ray emission command to be transmitted from the workstation 300 to the HVG 700 (see operation S1240 of FIG. 12), a time required for a high voltage to be applied from the HVG 700 to the X-ray emitter 200 (see operation S1250 of FIG. 12), and a time required for X-rays to be emitted by the X-ray emitter 200.

The X-ray emitter 200 may emit X-rays during an X-ray emission time 1300 determined by the workstation 300. The X-ray emission time 1300 may be an X-ray emission time that is preset by the workstation 300 according to an imaging protocol. In an embodiment, the X-ray emission time 1300 may be a time that is preset according to an APR protocol. For example, in a case of a chest AP protocol for imaging a patient's chest, the X-ray emission time 1300 may be 10 ms, and in a case of the pelvis protocol for imaging a patient's pelvis, the X-ray emission time 1300 may be 100 ms.

In an embodiment, the X-ray emission time 1300 may be a time determined by the workstation 300 according to an input received from the user.

The X-ray detector 100 may adjust the window time 1310 based on the X-ray emission time 1300 and the second latency Δ2 to the fourth latency Δ4. In an embodiment, the processor 130 (see FIG. 5) of the X-ray detector 100 may receive information about a setting value for the X-ray emission time 1300 from the workstation 300 (see FIG. 12) through the communication interface 120 (see FIG. 5), and identify the second time point $t_2$ at which the X-ray emission time 1300 ends, based on the received information about the setting value. The processor 130 may determine, as the end time point of the window time 1310 of the X-ray detector 100, a fifth time point $t_5$ at which the second latency Δ2 to the fourth latency Δ4 have elapsed from the second time point $t_2$ at which the X-ray emission time 1300 ends.

The second latency Δ2 may refer, for example, to a time required for all remaining X-rays (X-ray tails) to dissipate after X-rays are cut off by the HVG 700. In the embodiment illustrated in FIG. 13, the second latency Δ2 may be a time from the second time point $t_2$ to the third time point $t_3$.

The third latency Δ3 may refer, for example, to a time required for afterglow to dissipate from the scintillator 112 (see FIG. 5) in the X-ray receiver 110 (see FIG. 5) of the X-ray detector 100. In the embodiment illustrated in FIG. 13, the third latency Δ3 may be a time from the third time point $t_3$ to the fourth time point $t_4$.

The fourth latency Δ4 may refer, for example, to a time required for an electron-hole pair to be formed inside a PIN diode among the components of the photo sensor 114 (see FIG. 5) in the X-ray receiver 110 and to change a source potential of a TFT. In the embodiment illustrated in FIG. 13, the fourth latency Δ4 may be a time from the fourth time point $t_4$ to the fifth time point $t_5$.

Detailed descriptions of each of the second latency Δ2 to the fourth latency Δ4 and a method, performed by the processor 130, of obtaining information about the second latency Δ2 to the fourth latency Δ4 are the same as or similar to those provided above with reference to FIG. 8, and thus, redundant descriptions may not be repeated here.

The processor 130 of the X-ray detector 100 may perform a read-out during a readout time 1320 from the fifth time point $t_5$ at which the window time 1310 ends.

The X-ray detector 100 operating according to the timing chart 1300T illustrated in FIG. 13 may receive information about the X-ray emission time 1300 from the workstation 300, and determine, as the end time point of the window time 1310, the fifth time point $t_5$ at which the latencies (e.g., the second latency Δ2 to the fourth latency Δ4) have elapsed from the second time point $t_2$ at which the X-ray emission time 1300 ends. The X-ray detector 100 according to the embodiment of FIG. 13 adjusts the window time 1310 considering different X-ray emission times 1300 for imaging target areas (e.g., chest or pelvis), thereby reducing a time required for X-ray imaging and minimizing and/or reducing deterioration in X-ray image quality due to a dark current or electron traps.

Figure 14:
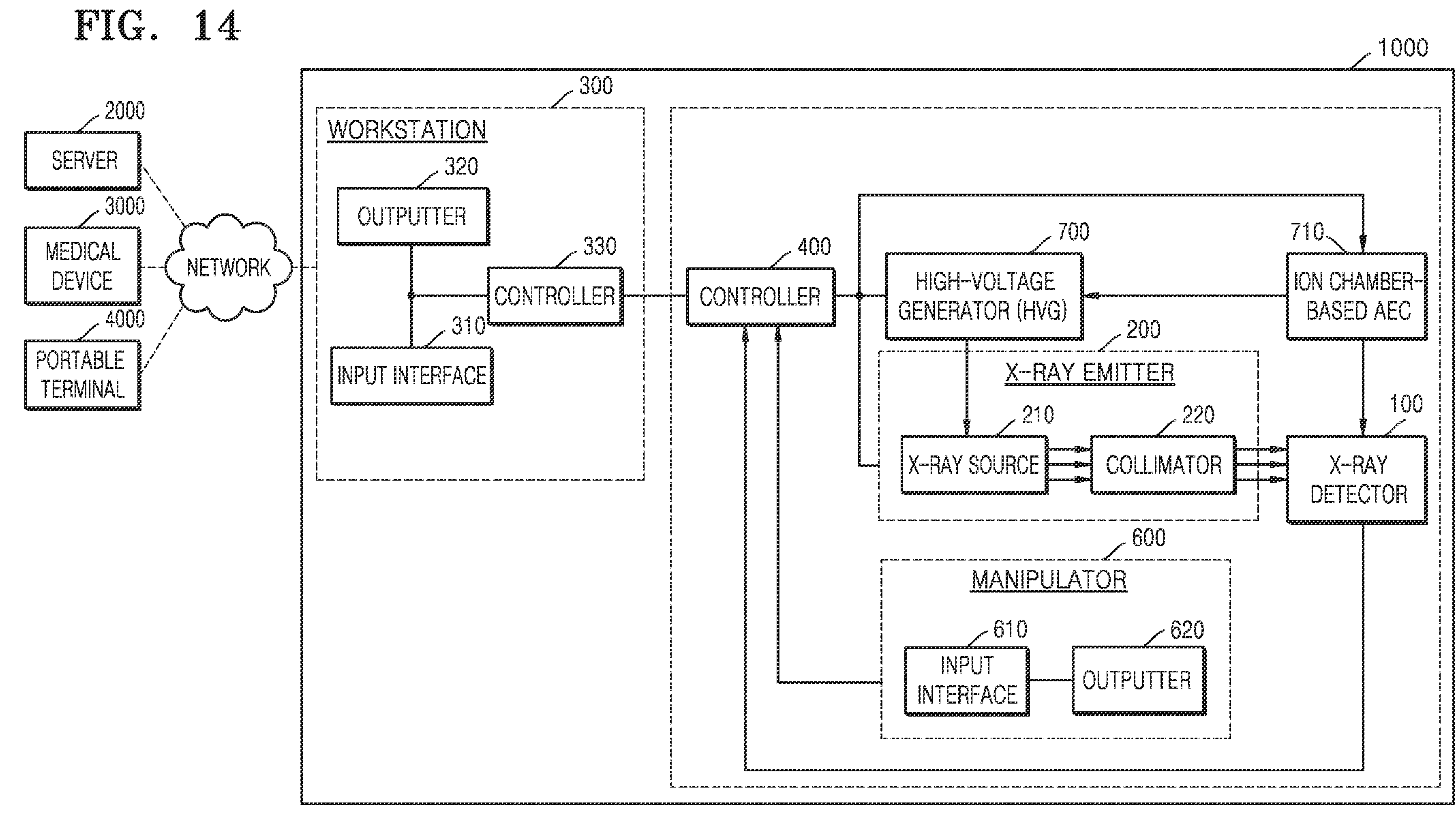
FIG. 14 is a block diagram illustrating an example configuration of an X-ray imaging device according to various embodiments.

FIG. 14 is a block diagram illustrating an example configuration of the X-ray imaging device 1000 according to various embodiments.

The X-ray imaging device 1000 illustrated in FIG. 14 may be implemented as a stationary X-ray device or a mobile X-ray device. The X-ray imaging device 1000 may include the X-ray detector 100, the X-ray emitter 200, the workstation 300, the controller (e.g., including various control and/or processing circuitry) 400, a manipulator (e.g., including various circuitry) 600, the HVG 700, and the ion chamber-based AEC device 800. Although not illustrated in FIG. 14, the X-ray imaging device 1000 may further include the communication interface (e.g., including communication circuitry) 500 (see FIG. 1) configured to transmit and receive data to and from the workstation 300. In an embodiment, the X-ray imaging device 1000 may be connected to an external device (e.g., the external server 2000, the medical device 3000, or the portable terminal 4000 (e.g., a smart phone, a tablet PC, or a wearable device)) to transmit and receive data to and from the external device.

The X-ray detector 100 detects X-rays that have been emitted from the X-ray emitter 200 and passed through an object. The X-ray detector 100 may be a digital detector. The X-ray detector 100 may be implemented using a TFT or a charge-coupled device (CCD). FIG. 14 illustrates that the X-ray detector 100 is included in the X-ray imaging device 1000, but the present disclosure is not limited thereto. In an embodiment, the X-ray detector 100 may be a separate device that may be connected to the X-ray imaging device 1000. In an embodiment, the X-ray detector 100 may be a mobile detector.

The X-ray emitter 200 may include an X-ray source 210 configured to generate X-rays by receiving a high voltage generated by the HVG 700, and emit the X-rays, and a collimator 220 configured to adjust an X-ray emission area by guiding, to a path, the X-rays emitted from the X-ray source 210.

The X-ray source 210 may include an X-ray tube, and the X-ray tube may be implemented as a two-pole vacuum tube with an anode and a cathode. A high vacuum of about 10 mmHg is created inside the X-ray tube, and the filament of the cathode is heated to a high temperature to generate thermal electrons. A tungsten filament may be used as the filament, and the filament may be heated by applying a voltage of 10 V and a current of about 3 A to about 5 A to an electric wire connected to the filament.

In addition, when a high voltage of about 10 kVp to about 300 kVp is applied between the cathode and the anode, the thermal electrons are accelerated to collide with a target material of the anode and generate X-rays. The generated X-rays are emitted to the outside through a window, and a berium thin film may be used as a material for the window. Here, most of the energy of the electrons colliding with the target material is consumed as heat, and the remaining energy is converted into X-rays.

The anode may mainly be formed of copper, the target material is arranged on a side facing the cathode, high-resistance materials such as Cr, Fe, Co, Ni, W, or Mo may be used as the target material. The target material may be rotated by a rotating magnetic field, and when the target material is rotated, an electron impact area may increase and the heat accumulation rate may increase more than 10 times per unit area compared to when the target material is fixed.

The voltage applied between the cathode and the anode of the X-ray tube is referred to as a tube voltage and is applied from the HVG 700, and its magnitude may be expressed in kVp of a peak value. As the tube voltage increases, the velocity of the thermal electrons increases, and as a result, the energy of X-rays (the energy of photons) generated as the thermal electrons collide with the target material increases. A current flowing in the X-ray tube is referred to as a tube current and may be expressed in mA of an average value, and as the tube current increases, the number of thermal electrons emitted from the filament increases, and as a result, the dose of X-rays (the number of X-ray photons) generated as the thermal electrons collide with the target material increases.

Thus, the energy of X-rays may be controlled by the tube voltage, and the intensity or dose of X-rays may be controlled by the tube current and the X-ray window time.

FIG. 14 illustrates that the workstation 300 is a component included in the X-ray imaging device 1000, but the present disclosure is not limited thereto. In an embodiment, the workstation 300 may be a component separate from the X-ray imaging device 1000, and may be arranged in a space physically separate from the X-ray imaging device 1000. In this case, the workstation 300 and the X-ray imaging device 1000 may be connected to each other in a wired or wireless manner, and when they are connected to each other in a wireless manner, the workstation 300 may further include a device (not shown) for synchronizing their clocks with each other.

The workstation 300 may include the input interface 310, an outputter 320, and a controller 330. The outputter 320 and the input interface 310 provide a user with interfaces for operating the workstation 300 and the X-ray imaging device 1000.

The X-ray imaging device 1000 may be controlled through the workstation 300 and may also be controlled by the controller 400. Accordingly, the user may control the X-ray imaging device 1000 by controlling the X-ray imaging device 1000 through the workstation 300, or may control the X-ray imaging device 1000 through the controller 400 and manipulator 600 both included in the X-ray imaging device 1000. In other words, the user may remotely control the X-ray imaging device 1000 through the workstation 300, or may directly control the X-ray imaging device 1000.

FIG. 14 illustrates that the controller 330 of the workstation 300 and the controller 400 of the X-ray imaging device 1000 are separate from each other, but this is merely an implementation example, and the present disclosure is not limited to the configuration illustrated in FIG. 14. In an embodiment, the controllers 330 and 400 may be implemented as one integrated controller.

Each of the input interface 310 and the outputter 320 of the workstation 300, and the input interface 610 and outputter 620 of the X-ray imaging device 1000 may provide the user with an interface for manipulating the X-ray imaging device 1000. FIG. 14 illustrates that the workstation 300 and the X-ray imaging device 1000 include the input interfaces 310 and 610 and the outputters 320 and 620, respectively, but the present disclosure is not limited thereto. The outputter or input interface may be implemented in only one of the workstation 300 and the X-ray imaging device 1000.

Examples of the input interfaces 310 and 610 may include a keyboard, a mouse, a touch screen, a speech recognizer, a fingerprint recognition device, an iris recognition device, and other input devices known to those of skill in the art. The user may input a command for X-ray emission through the input interface 310 or 610, and the input interface 310 or 610 may include a switch for inputting such a command. The switch may be provided such that an emission command for X-ray emission may be input only when the switch is pressed twice.

The switch may have a structure in which, when the user presses the switch, a preparation command to perform preheating for X-ray emission is input, and when the user further presses the switch, an emission command for actual X-ray emission is input. When the user manipulates the switch in this way, the controller 330 or 400 generates a signal corresponding to the command input through the switch manipulation, that is, a preparation signal, and transmit the signal to the HVG 700 to generate a high voltage for generating X-rays.

The controller 400 may include various circuitry and control the overall operation of the X-ray imaging device 1000.

The manipulator 600 may include various circuitry and provides an interface for manipulating the X-ray imaging device 1000. The manipulator 600 may include the input interface 610 and the outputter 620. The input interface 610 may receive, from the user, a command for manipulating the X-ray imaging device 1000, and various pieces of information about X-ray imaging. The controller 400 may control or manipulate the X-ray imaging device 1000 based on information input to the input interface 610. The outputter 620 may output a sound indicating imaging-related information such as X-ray emission, under control of the controller 400.

The HVG 700 generates a high voltage for generating X-rays and applies the high voltage to the X-ray source 210. In an embodiment, the HVG 700 starts preheating upon receiving an X-ray emission preparation signal transmitted from the controller 330 or 400, and when the preheating is completed, transmits an X-ray emission preparation completion signal to the controller 330 of the workstation 300, or the controller 400. In addition, the X-ray detector 100 also needs to prepare for X-ray detection in order to detect X-rays, the controller 330 or 400 transmits an X-ray emission preparation signal to the X-ray detector 100 such that the X-ray detector 100 may prepare to detect X-rays that have passed through an object, in addition to the preheating of the HVG 700. When the X-ray detector 100 receives the X-ray emission preparation signal, the X-ray detector 100 prepares to detect X-rays, and when the preparation for detection is completed, transmits a detection preparation completion signal to the controller 330 of the workstation 300, or the controller 400.

Preheating of the HVG 700 is completed, preparation of the X-ray detector 100 for X-ray detection is completed, the controller 330 or 400 transmits an X-ray emission signal to the HVG 700, the HVG 700 generates a high voltage and applies the high voltage to the X-ray source 210, and the X-ray source 210 emits X-rays.

When transmitting the X-ray emission signal, the controller 330 or 400 may transmit a sound output signal to the outputter 320 or 620 to output a predetermined sound such that the object may be aware of the X-ray emission. In addition, the outputter 320 or 620 may output a sound indicating imaging-related information other than the X-ray emission. FIG. 14 illustrates that the outputter 620 is included in the manipulator 600, but the present disclosure is not limited thereto. In an embodiment, the outputter 620 or part of the outputter 620 may be located at a different point from where the manipulator 600 is located. For example, it may be located on a wall of an imaging room where X-ray imaging of an object is performed.

The controller 330 or 400 controls the positions of the X-ray emitter 200 and the X-ray detector 100, an imaging timing, and imaging conditions according to imaging conditions that are set by the user.

For example, the controller 330 or 400 controls the HVG 700 and the X-ray detector 100 to control a timing for emit X-rays, the intensity of the X-rays, and an emission area of the X-rays, and the like, according to a command input through the input interface 310 or 610. In addition, the controller 330 or 400 adjusts the position of the X-ray detector 100 and control an operation timing of the X-ray detector 100 according to predetermined imaging conditions.

In addition, the controller 330 or 400 generates a medical image of an object using image data received through the X-ray detector 100. For example, the controller 330 or 400 may generate a medical image of the object by receiving image data from the X-ray detector 100, removing noise from the image data, and adjusting the dynamic range and interleaving.

The outputter 320 or 620 may output the medical image generated by the controller 330 or 400. The outputter 320 or 620 may output information necessary for the user to manipulate the X-ray imaging device 1000, such as a user interface (UI), user information, or object information. Examples of the outputters 320 and 620 may include speakers, printers, cathode-ray tube (CRT) displays, liquid-crystal displays (LCDs), plasma display panel (PDP) displays, organic light-emitting diode (OLED) displays, field-emission displays (FEDs), light-emitting diode (LED) displays, vacuum fluorescent displays (VFDs), digital light processing (DLP) displays, field-emission displays (FEDs), three-dimensional displays, transparent displays, and various output devices within the range that will be apparent to those of skill in the art.

The workstation 300 illustrated in FIG. 14 may further include the communication interface 500 (see FIG. 1) that may be connected to the server 2000, the medical device 3000, the portable terminal 4000, and the like through a network.

The communication interface 500 may be connected to the network in a wired or wireless manner to perform communication with the external server 2000, the external medical device 3000, or the external portable terminal 4000. The communication interface 500 may transmit and receive data related to diagnosis of an object through the network, and may also transmit and receive medical images captured by other medical devices 3000, such as computed tomography (CT), magnetic resonance imaging (MRI), and X-ray devices. Furthermore, the communication interface 500 may receive a diagnosis history or a treatment schedule of a patient from the server 2000, and use it to diagnose an object. In addition, the communication interface 500 may perform data communication not only with the server 2000 or the medical device 3000 within a hospital, but also with portable terminals 4000 such as mobile phones, personal digital assistants (PDAs), and notebook computers of doctors or clients.

The communication interface 500 may include various communication circuitry including one or more components configured to enable communication with an external device, and may include, for example, a short-range communication module, a wired communication module, and a wireless communication module.

The short-range communication module refers to a module configured to perform short-range communication with a device located within a predetermined distance. Examples of short-range communication techniques according to an embodiment of the present disclosure may include wireless LAN, Wi-Fi, Bluetooth, ZigBee, WFD, UWB, Infrared Data Association (IrDA), BLE, near-field communication (NFC), and the like, but are not limited thereto.

The wired communication module may refer, for example, to a module including various circuitry for communication using electric signals or optical signals, and examples of wired communication techniques may include wired communication techniques using pair cables, coaxial cables, optical fiber cables, and other wired communication techniques that will be apparent to those of skill in the art.

The wireless communication module may include various circuitry and transmits and receives wireless signals to and from at least one of a base station, an external device, and a server on a mobile communication network. Here, examples of wireless signals may include a voice call signal, a video call signal, or various types of data according to text/multimedia message transmission and reception.

The X-ray imaging device 1000 illustrated in FIG. 14 may include a plurality of DSPs, ultra-small arithmetic processing devices, processing circuits for special purposes (e.g., high-speed A/D conversion, fast Fourier transform, or array processing), and the like.

The present disclosure provides a method for variably adjusting a window time of the X-ray detector 100. An operation method of the X-ray detector according to an example embodiment of the present disclosure may include: obtaining information about an X-ray emission end time point based on an X-ray emission end signal received from an automatic exposure control (AEC) device or a setting value for an X-ray emission time received from a workstation; adjusting a window time for the X-ray detector to receive X-rays that have passed through an object, based on the information about the X-ray emission end time point; in response to the window time being ended, obtaining X-ray image data by performing a readout.

In an example embodiment of the present disclosure, the obtaining of the information about the X-ray emission end time point may include receiving an X-ray emission end signal from the ion chamber-based AEC device arranged outside the X-ray detector.

In an example embodiment of the present disclosure, the obtaining of the information about the X-ray emission end time point may include receiving the X-ray emission end signal from the HVG. The X-ray emission end signal may be transmitted from the ion chamber-based AEC device arranged outside the X-ray detector to the HVG, and is transmitted from the HVG to the X-ray detector.

In an example embodiment of the present disclosure, the obtaining of the information about the X-ray emission end time point may include obtaining the X-ray emission end signal by monitoring a voltage value measured by a pixel-related AEC or an AEC-related photodiode included in the X-ray detector and configured to detect X-rays.

In an example embodiment of the present disclosure, the obtaining of the information about the X-ray emission end time point may include: receiving, from the workstation, setting value information about the X-ray emission time according to an imaging protocol, and obtaining the information about the X-ray emission end time point based on the setting value information about the X-ray emission time.

In an example embodiment of the present disclosure, the adjusting of the window time may include: determining an end time point of the window time based on a time point at which an X-ray emission preparation signal is received from the workstation, a delay time due to signal transmission and reception between the workstation and the HVG, and the X-ray emission time.

In an example embodiment of the present disclosure, the adjusting of the window time may include determining an end time point of the window time based on the information about the X-ray emission end time point and a delay time due to the HVG and the X-ray detector.

In an example embodiment of the present disclosure, the delay time may include at least one of a first delay time required for remaining X-rays in an X-ray tube in the HVG to dissipate after receiving the X-ray emission end signal, a second delay time required for afterglow of a scintillator in the X-ray detector to dissipate, and a third delay time required for electron-hole pairs to form and change a potential. The determining of the end time point of the window time may include determining, as the end time point of the window time, a time point at which the delay time has elapsed after the X-ray emission end time point.

In an example embodiment of the present disclosure, the delay time may include at least one of the first delay time, the second delay time, the third delay time, and a fourth delay time required to receive the X-ray emission end signal from the AEC device or the HVG.

In an example embodiment of the present disclosure, the obtaining of the X-ray image data may include performing a readout after the end time point of the window time.

The present disclosure provides the X-ray detector 100 for variably adjusting a window time. The X-ray detector according to an example embodiment of the present disclosure may include: an X-ray receiver configured to detect X-rays that have passed through an object, and converting the detected X-rays into electric signals, a communication interface comprising communication circuitry configured to perform data communication with an automatic exposure control (AEC) device, a high-voltage generator (HVG), and/or a workstation, a memory storing at least one instruction, and at least one processor, comprising processing circuitry, individually and/or collectively configured to execute the at least one instruction stored in the memory to: obtain information about an X-ray emission end time point based on an X-ray emission end signal received from the AEC device through the communication interface, or a setting value for an X-ray emission time received from the workstation; adjust a window time for the X-ray detector to receive X-rays that have passed through the object, based on the information about the X-ray emission end time point; and in response to the window time being ended, obtain X-ray image data by performing a readout.

In an example embodiment of the present disclosure, at least one processor, individually and/or collectively, may be configured to receive an X-ray emission end signal from the ion chamber-based AEC device arranged outside the X-ray detector, through the communication interface.

In an example embodiment of the present disclosure, at least one processor, individually and/or collectively, may be configured to receive an X-ray emission end signal from the HVG through the communication interface. The X-ray emission end signal may be transmitted from the ion chamber-based AEC device arranged outside the X-ray detector to the HVG, and is transmitted from the HVG to the X-ray detector.

In an example embodiment of the present disclosure, the X-ray detector may further include an internal AEC device configured to detect X-rays received by the X-ray detector, and output a signal charge according to the amount of the detected X-rays. At least one processor, individually and/or collectively, may be configured to obtain the X-ray emission end signal by monitoring a voltage value of the signal charge output by the internal AEC device.

In an example embodiment of the present disclosure, at least one processor, individually and/or collectively, may be configured to: receive setting value information about the X-ray emission time according to an imaging protocol, from the workstation through the communication interface, and obtain the information about the X-ray emission end time point based on the setting value information about the X-ray emission time.

In an example embodiment of the present disclosure, at least one processor, individually and/or collectively, may be configured to determine an end time point of the window time based on a time point at which an X-ray emission preparation signal is received from the workstation, a delay time due to signal transmission and reception between the workstation and the HVG, and the X-ray emission time.

In an example embodiment of the present disclosure, at least one processor, individually and/or collectively, may be configured to determine an end time point of the window time based on the information about the X-ray emission end time point and a delay time due to the HVG and the X-ray detector.

In an example embodiment of the present disclosure, the delay time may include at least one of a first delay time required for remaining X-rays in an X-ray tube in the HVG to dissipate after receiving the X-ray emission end signal, a second delay time required for afterglow of a scintillator in the X-ray detector to dissipate, and a third delay time required for electron-hole pairs to form and change a potential, and at least one processor, individually and/or collectively, may be configured to determine, as the end time point of the window time, a time point at which the delay time has elapsed after the X-ray emission end time point.

In an example embodiment of the present disclosure, the delay time may include at least one of the first delay time, the second delay time, the third delay time, and a fourth delay time required to receive the X-ray emission end signal from the AEC device or the HVG.

According to an example embodiment of the present disclosure, provided is a computer program product including a non-transitory computer-readable storage medium having recorded thereon a program to be executed by a computer. The storage medium may include instructions, which when executed, cause an X-ray detector to perform operations including: obtaining information about an X-ray emission end time point based on an X-ray emission end signal received from an AEC device or a setting value for an X-ray emission time received from the workstation; adjusting a window time for the X-ray detector to receive X-rays that have passed through an object, based on the information about the X-ray emission end time point; and in response to the window time being ended, obtaining X-ray image data by performing a readout.

A program executable by the X-ray detector 100 or the X-ray imaging device 1000 described herein may be implemented as a hardware component, a software component, and/or a combination of hardware components and software components. The program is executable by any system capable of executing computer-readable instructions.

The software may include a computer program, code, instructions, or a combination of one or more thereof, and may configure the processor to operate as desired or may independently or collectively instruct the processor.

The software may be implemented as a computer program that includes instructions stored in computer-readable storage media. The computer-readable storage media may include, for example, magnetic storage media (e.g., ROM, RAM, floppy disks, hard disks, etc.) and optical storage media (e.g., a compact disc ROM (CD-ROM), a digital versatile disc (DVD), etc.). The computer-readable recording medium may be distributed in computer systems connected via a network and may store and execute computer-readable code in a distributed manner. The medium may be readable by a computer, stored in a memory, and executed by a processor.

The computer-readable storage medium may be provided in the form of a non-transitory storage medium. The 'non-transitory' storage medium is a tangible device, and may not include a signal, but this term does not differentiate between where data is semi-permanently stored in the storage medium and where the data is temporarily stored in the storage medium. For example, the non-transitory storage medium may include a buffer in which data is temporarily stored.

In addition, a program according to embodiments disclosed herein may be provided in a computer program product. The computer program product may be traded as commodities between sellers and buyers.

The computer program product may include a software program and a computer-readable recording medium storing the software program. For example, the computer program product may include a product (e.g., a downloadable application) in the form of a software program electronically distributed through a manufacturer of the electronic device or an electronic market (e.g., Samsung Galaxy Store). For electronic distribution, at least part of the software program may be stored in a storage medium or temporarily generated. In this case, the storage medium may be a storage medium of a server or relay server that temporarily stores the software program.

The computer program product may include a storage medium of the X-ray detector 100, in the X-ray detector 100 and/or the X-ray imaging device 1000 including the X-ray detector 100. Alternatively, when there is a third device (e.g., a mobile device) communicating with the X-ray detector 100, the computer program product may include a storage medium of the third device. Alternatively, the computer program product may include a software program, which is transmitted from the X-ray detector 100 to the third device or transmitted from the third device to the X-ray detector 100.

In this case, any one of the X-ray detector 100 or the X-ray imaging device 1000 may execute the computer program product to perform the method according to the disclosed embodiments. Alternatively, two or more of the X-ray detector 100, the X-ray imaging device 1000, and the third device may execute the computer program product to execute the method according to the disclosed embodiments in a distributed manner.

For example, the X-ray detector 100 may execute the computer program product stored in the memory 140 (see FIG. 5) to control another electronic device (e.g., a mobile device) communicatively connected to the X-ray detector 100 to perform the method according to the disclosed embodiments.

As another example, the third device may execute the computer program product to control an electronic device communicatively connected to the third device to perform the method according to the disclosed embodiments.

When the third device executes the computer program product, the third device may download the computer program product from the X-ray detector 100 and execute the downloaded computer program product. Alternatively, the third device may execute the computer program product provided in a pre-loaded state to perform the methods according to the disclosed embodiments.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. A method of operating an X-ray detector, the method comprising:

obtaining information about an X-ray emission end time point based on an X-ray emission end signal received from an automatic exposure control (AEC) device or a setting value for an X-ray emission time received from a workstation;

adjusting a window time for the X-ray detector to receive X-rays that have passed through an object, based on the information about the X-ray emission end time point and information about a delay time due to a high-voltage generator (HVG) and the X-ray detector; and in response to the window time being ended, obtaining X-ray image data by performing a readout, wherein the delay time comprises at least one of a first delay time required for remaining X-rays in an X-ray tube in the HVG to dissipate after receiving the X-ray emission end signal, a second delay time required for afterglow of a scintillator in the X-ray detector to dissipate, and a third delay time required for electron-hole pairs to form and change a potential.

2. The method of claim 1, wherein the obtaining of the information about the X-ray emission end time point comprises receiving an X-ray emission end signal from the HVG, and the X-ray emission end signal is transmitted from an ion chamber-based automatic exposure control (AEC) device arranged outside the X-ray detector to the HVG, and is transmitted from the HVG to the X-ray detector.

3. The method of claim 1, wherein the obtaining of the information about the X-ray emission end time point comprises obtaining an X-ray emission end signal by monitoring a voltage value measured by a pixel-related automatic exposure control (AEC) device or an AEC device-related photodiode, included in the X-ray detector and configured to detect X-rays.

4. The method of claim 1, wherein the obtaining of the information about the X-ray emission end time point comprises:

receiving, from the workstation, setting value information about the X-ray emission time according to an imaging protocol; and obtaining the information about the X-ray emission end time point based on the setting value information about the X-ray emission time.

5. The method of claim 4, wherein the adjusting of the window time comprises determining an end time point of the window time based on a time point at which an X-ray emission preparation signal is received from the workstation, a delay time due to signal transmission and reception between the workstation and the HVG, and the X-ray emission time.

6. The method of claim 1, wherein the end time point of the window time is determined based on the information about the X-ray emission end time point and the information about the delay time.

7. The method of claim 6, wherein the determining of the end time point of the window time comprises determining, as the end time point of the window time, a time point at which the delay time has elapsed after the X-ray emission end time point.

8. An X-ray detector comprising:

an X-ray receiver configured to detect X-rays that have passed through an object, and converting the detected X-rays into electric signals;

a communication interface comprising communication circuitry configured to perform data communication with an automatic exposure control (AEC) device, a high-voltage generator (HVG), or a workstation;

a memory storing at least one instruction; and at least one processor, comprising processing circuitry, individually and/or collectively, configured to execute the at least one instruction stored in the memory, wherein at least one processor is configured to:

obtain information about an X-ray emission end time point based on an X-ray emission end signal received from the AEC device through the communication interface, or a setting value for an X-ray emission time received from the workstation;

adjust a window time for the X-ray detector to receive X-rays that have passed through the object, based on the information about the X-ray emission end time point and information about a delay time due to a high-voltage generator (HVG) and the X-ray detector; and in response to the window time being ended, obtain X-ray image data by performing a readout, wherein the delay time comprises at least one of a first delay time required for remaining X-rays in an X-ray tube in the HVG to dissipate after receiving the X-ray emission end signal, a second delay time required for afterglow of a scintillator in the X-ray detector to dissipate, and a third delay time required for electron-hole pairs to form and change a potential.

9. The X-ray detector of claim 8, wherein at least one processor, individually and/or collectively, is configured to receive an X-ray emission end signal from the HVG through the communication interface, wherein the X-ray emission end signal is transmitted from an ion chamber-based automatic exposure control (AEC) device arranged outside the X-ray detector to the HVG, and is transmitted from the HVG to the X-ray detector.

10. The X-ray detector of claim 8, further comprising an internal automatic exposure control (AEC) device configured to detect X-rays received by the X-ray detector, and output a signal charge according to an amount of the detected X-rays, wherein at least one processor, individually and/or collectively, is configured to obtain an X-ray emission end signal by monitoring a voltage value of the signal charge that is output by the internal AEC device.

11. The X-ray detector of claim 8, wherein at least one processor, individually and/or collectively, is configured to: receive setting value information about the X-ray emission time according to an imaging protocol, from the workstation through the communication interface, and obtain the information about the X-ray emission end time point based on the setting value information about the X-ray emission time.

12. The X-ray detector of claim 11, wherein at least one processor, individually and/or collectively, is configured to determine an end time point of the window time based on a time point at which an X-ray emission preparation signal is received from the workstation, a delay time due to signal transmission and reception between the workstation and the HVG, and the X-ray emission time.

13. The X-ray detector of claim 8, wherein at least one processor, individually and/or collectively, is configured to determine the end time point of the window time based on the information about the X-ray emission end time point and the information about the delay time.

14. The X-ray detector of claim 13, wherein the at least one processor, individually and/or collectively, is configured to determine, as the end time point of the window time, a time point at which the delay time has elapsed after the X-ray emission end time point.

15. A computer program product comprising a non-transitory computer-readable storage medium having recorded thereon instructions for performing an operation method of an X-ray detector, the operation method comprising:

obtaining information about an X-ray emission end time point based on an X-ray emission end signal received from an automatic exposure control (AEC) device or a setting value for an X-ray emission time received from a workstation;

adjusting a window time for the X-ray detector to receive X-rays that have passed through an object, based on the information about the X-ray emission end time point and information about a delay time due to a high-voltage generator (HVG) and the X-ray detector; and in response to the window time being ended, obtaining X-ray image data by performing a readout, wherein the delay time comprises at least one of a first delay time required for remaining X-rays in an X-ray tube in the HVG to dissipate after receiving the X-ray emission end signal, a second delay time required for afterglow of a scintillator in the X-ray detector to dissipate, and a third delay time required for electron-hole pairs to form and change a potential.

* * * * *